US012715854B2

(12) United States Patent
Chlopicki et al.

(10) Patent No.: US 12,715,854 B2
(45) **Date of Patent: *Aug. 25, 2026**

(54) AROMATIC SULPHONAMIDES DERIVATIVES THAT INHIBITS PDI A3, THEIR SYNTHESIS AND USE

(71) Applicant: Uniwersytet Jagiellonski, Cracow (PL)

(72) Inventors: Stefan Chlopicki, Cracow (PL); Ivars Kalvins, Riga (LV); Kamil Przyborowski, Cracow (PL); Marta Stojak, Cracow (PL); Victor Andrianov, Riga (LV); Ilona Domraceva, Riga (LV); Iveta Kanepe-Lapsa, Riga (LV); Diana Zelencova, Riga (LV); Joanna Wietrzyk, Wrocław (PL); Eliza Turlej, Wrocław (PL); Martyna Stachowicz, Wrocław (PL); Joanna Jarosz, Wrocław (PL); Magdalena Milczarek, Wrocław (PL); Karol Kramkowski, Białystok (PL)

(73) Assignee: Uniwersytet Jagiellonski, Cracow (PL)

( * ) Notice: Subject to any disclaimer, the term of this patent is extended or adjusted under 35 U.S.C. 154(b) by 979 days.

This patent is subject to a terminal disclaimer.

(21) Appl. No.: 17/791,657

(22) PCT Filed: Jan. 10, 2020

(86) PCT No.: PCT/PL2020/050005
§ 371 (c)(1),
(2) Date: Jul. 8, 2022

(87) PCT Pub. No.: WO2021/141507
PCT Pub. Date: Jul. 15, 2021

(65) Prior Publication Data

US 2023/0069886 A1 Mar. 9, 2023

(51) Int. Cl.

| | |
|---|---|
| ***C07D 203/24*** | (2006.01) |
| ***A61P 7/02*** | (2006.01) |
| ***C07D 401/12*** | (2006.01) |
| ***C07D 403/12*** | (2006.01) |
| ***C07D 413/12*** | (2006.01) |

(52) U.S. Cl.
CPC .............. *C07D 401/12* (2013.01); *A61P 7/02* (2018.01); *C07D 203/24* (2013.01); *C07D 403/12* (2013.01); *C07D 413/12* (2013.01)

(58) Field of Classification Search
CPC .................................................... C07D 203/24
See application file for complete search history.

(56) References Cited

U.S. PATENT DOCUMENTS

| | | | |
|---|---|---|---|
| 4,267,174 | A | 5/1981 | Berger et al. |
| 2008/0242677 | A1 | 10/2008 | Dehmlow et al. |

FOREIGN PATENT DOCUMENTS

| | | |
|---|---|---|
| WO | 2016/118639 A1 | 7/2016 |

OTHER PUBLICATIONS

CA Reg. No. 2374240-61-4, entered into STN on Sep. 5, 2019.*
RN 1065144-08-2 in CAS Registry, 2008.*
Baldwin J E et al: "Amino Acid Synthesis via Ring Opening of N-Sulphonyl Ayiridine-2-Carboxylate Esters With Organometallic Reagents", Tetrahedron, Elsevier Science Publishers, Amsterdam, NL, vol. 49, No. 28, Jan. 1, 1993 (Jan. 1, 1993), pp. 6309-6330.
Lam et al: "Electronic Supplementary Information Intermolecular (4+3) Cycloadditions of Aziridinyl Enolsilanes", Dec. 16, 2013 (Dec. 16, 2013), pp. S1-S54.
Takeda et al: "Supporting Information Asymmetric Synthesis of b 2-Aryl Amino Acids through Pd-Catalyzed Enantiospecific and Regioselective Ring-Opening Suzuki-Miyaura Arylation of Aziridine-2-carboxylates", Jun. 3, 2019 (Jun. 3, 2019), pp. S1-S126.

* cited by examiner

*Primary Examiner* — Brian E McDowell
(74) *Attorney, Agent, or Firm* — Arrigo, Lee, Guttman & Mouta-Bellum LLP

(57) ABSTRACT

The invention relates to a new group of aromatic sulphonamides derivatives of formula (I) and their synthesis and use for modulation of the activity of protein disulfide isomerase (PDI). More particularly, the invention provides small molecule inhibitors of PDI A3 that display antiplatelet, antithrombotic and anticancer activities.

(I)

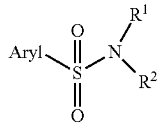

1 Claim, 4 Drawing Sheets

A

B

AROMATIC SULPHONAMIDES DERIVATIVES THAT INHIBITS PDI A3, THEIR SYNTHESIS AND USE

FIELD OF THE INVENTION

The invention relates to a new group of aromatic sulphonamides derivatives and their synthesis and use for modulation of the activity of protein disulfide isomerase (PDI). More particularly, the invention provides small molecule inhibitors of PDI A3 that display antiplatelet, antithrombotic and anticancer activities.

BACKGROUND OF THE INVENTION

Protein disulfide isomerase (PDI) is a thiol-oxidoreductase chaperone protein that is responsible for the isomerization, reduction, and oxidation of disulfide bonds. There are known over 20 members of the PDI family of enzymes. Structurally, prototypic PDI consists of four domains with a thioredoxin fold: a, b, b' and a', an extended C-terminus with KDEL ER retention sequence, and an interdomain linker x between the b' and a' domains. The a and a' domains are catalytically active, contain redox active CGHC active site and independently can perform oxidation and reduction reactions (Darby and Creighton, 1995). The b and b' domains are noncatalytic, but provide a substrate-binding domain of PDI. All four domains are needed to achieve the isomerization and chaperone activity of PDJ. Besides its catalytic role involving thiols and disulfides, PDI also serves an essential structural role as the beta subunit of prolyl-4-hydroxylase (Koivu et al., 1987) and as a microsomal triglyceride transfer protein (Wetterau et al., 1990).

Protein disulfide isomerase (PDI) catalyze posttranslational disulfide bond formation and exchange and serve as chaperones during protein folding (Hatahet et al., 2009). PDI has been also identified at many diverse subcellular locations outside the endoplasmic reticulum. It has biological functions on the cell surfaces of lymphocytes, hepatocytes, platelets, and endothelial cells (Manickam et al., 2008; Hotchkiss et al., 1998; Essex et al., 1999; Burgess et al., 2000; Bennett et al., 2000; Hotchkiss et al., 1998; Burgess et al., 2000). PDI is rapidly secreted from both endothelial cells and platelets during thrombus formation in vivo (Cho et al., 2008; Jasuja et al., 2010). Inhibition of PDI using neutralizing antibodies blocks thrombus formation in several thrombosis models (Bennett et al., 2000; Cho et al., 2008; Jasuja et al., 2010; Reinhardt et al. 2008). Inhibition of PDI in these models abrogates not only platelet accumulation at the injury site but also fibrin generation. Although number of studies focused on PDIA1, this isoform is not the sole isoform of PDI that support thrombosis in vivo and platelet aggregation in vitro. In particular, PDIA3 has an important role in the activation of the αIIbβ3 fibrinogen receptor and platelet aggregation that cannot be replaced by PDIA1 (Essex D W and Wu Yi 2018). Thus, deficiency of PDI A3 results in blunted platelet aggregation (Essex D W and Wu Yi 2018) due to the impaired activation of GpIIb/IIIa receptor that is a major platelet receptor for fibrinogen binding and is required for platelet aggregation and thrombus formation (Essex D W and Wu Yi 2018).

Importantly, PDI has been implicated in proliferation, survival and metastasis of several types of cancers (Lee et al, 2017, Xu et al., 2012; Hashida et al., 2011; Lovat et al., 2008) and the important role of PDIA3 was postulated (Yang Z et al., 2018; Hettinghouse A et al., 2018).

These observations demonstrate a critical role for PDIA3 in various pathologies (Cho et al., 2008) including thrombus formation and development of cancer. In particular, PDI A3 is a novel interesting target to develop antiplatelet, antithrombotic effects and anticancer therapeutics Several patent documents provide compounds that inhibit enzyme activity of cell-associated protein disulfide isomerase e.g. US20160145209A1, WO2016118639, US20150133514A1, US20020115713A1, WO2017011890A1, but none of them relates to aromatic sulphonamides derivatives.

Presently, majority of available inhibitors of PDI are sulfhydryl-reactive compounds that bind covalently and are non-selective, acting broadly on thiol isomerases (Karala et al., 2010) or are cytotoxic (Lovat et al., 2008; Khan et al., 2011). Thus, there is a clear need for new agents that interfere with PDI A3 activity but are otherwise selective and well tolerated in therapeutic contexts. Now it has been found that some of among N,N-disubstituted aromatic sulphonamides possess unique pharmacological properties associated with their ability to inhibit PDIA3 activity, which property affords their antiplatelet, antithrombotic, and anticancer activities.

DETAILED DESCRIPTION OF THE INVENTION

The invention relates to N,N-disubstituted aromatic sulphonamides of formula (I) in form of racemates or enantiomers that inhibits PDI A3:

(I)

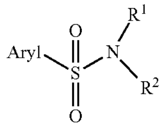

or a pharmaceutically acceptable salt and/or prodrug, wherein:

$R^1$ and $R^2$ taken together represent group of substituents consisting of formula (II)

(II)

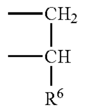

wherein $R^6$ represents: CN, $CONR^7R^8$, $COOR^9$, $COO^-Met^+$, $COR^{10}$,

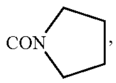, 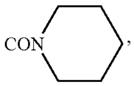, 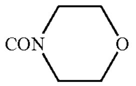

wherein:

$R^7$ and $R^8$ independently represent H or lower alkyl $C_1$-$C_4$, and $R^9$ and $R^{10}$ independently represent lower alkyl $C_1$-$C_4$;

$Met^+$ represents alkali metal cation $Li^+$, $Na^+$ or $K^+$ and wherein Aryl- represents: mono, di- or tri-substituted phenyl group of formula (III):

(III)

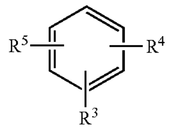

wherein $R^3$, $R^4$ and $R^5$ independently represent H, linear alkyl group $C_1$-$C_{12}$, O-alkyl $C_1$-$C_4$, branched alkyl $C_3$-$C_4$, cycloalkyl, phenyl, $NO_2$, halogen (Cl, F), trifluoromethyl, lower $C_1$-$C_4$ alkoxy, lower $C_1$-$C_4$ dialkylamino, lower $C_1$-$C_4$ acylamino;

or wherein Aryl- represents unsubstituted-, mono- and di-substituted-α-, β- and γ-naphthyl-group of formula IV:

(IV)

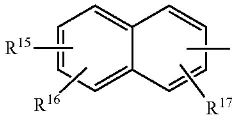

wherein:

$R^{15}$, $R^{16}$ and $R^{17}$ independently represent H, lower alkyl $C_1$-$C_4$, Cl, O-alkyl $C_1$-$C_4$, —CHO or $NR^{18}R^{19}$, wherein $R^{18}$ and $R^{19}$ independently represent H or lower alkyl $C_1$-$C_4$;

or wherein Aryl- represents pyridin-3-yl group of formula V:

(V)

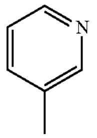

or 2-oxochromen-6-yl group of formula VI:

(VI)

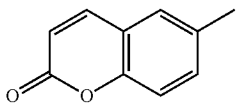

or 2-oxo-1H-quinolin-6-yl group of formula VII:

(VII)

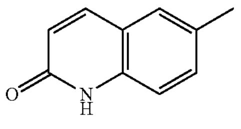

with the exception that the compound is not selected from the group comprising

Methyl 1-(p-tolylsulfonyl)aziridine-2-carboxylate (C-3161),

Methyl 1-(4-nitrophenyl)sulfonylaziridine-2-carboxylate (C-3212), 1-(p-Tolylsulfonyl)aziridine-2-carboxamide (C-3220), Methyl 1-(benzenesulfonyl)aziridine-2-carboxylate (C-3251), 1-(p-Tolylsulfonyl)aziridine-2-carbaldehyde (C-3262), 1-[1-(p-Tolylsulfonyl)aziridin-2-yl]ethanone (C-3263), Methyl 1-(4-chlorophenyl)sulfonylaziridine-2-carboxylate (C-3296), Methyl 1-(4-propylphenyl)sulfonylaziridine-2-carboxylate (C-3304), 1-(p-Tolylsulfonyl)aziridine-2-carbonitrile (C-3314), N,N-Dimethyl-1-(p-tolylsulfonyl)aziridine-2-carboxamide (C-3342).

Preferably, the invention relates to following derivatives of N,N-disubstituted aromatic sulphonamides that are chosen for the list:

Methyl 1-(benzenesulfonyl)aziridine-2-carboxylate;

Methyl 1-(4-butoxyphenyl)sulfonylaziridine-2-carboxylate;

1-(4-Nitrophenyl)sulfonylaziridine-2-carboxamide;

Methyl 1-(4-butylphenyl)sulfonylaziridine-2-carboxylate;

1-[1-(4-Butylphenyl)sulfonylaziridin-2-yl]ethanone;

Methyl 1-(p-tolylsulfonyl)aziridine-2-carboxylate;

Methyl 1-[[6-(dimethylamino)-1-naphthyl]sulfonyl]aziridine-2-carboxylate;

Methyl 1-[[6-(dimethylamino)-5-formyl-2-naphthyl]sulfonyl]aziridine-2-carboxylate;

Methyl 1-[[5-(dimethylamino)-2-naphthyl]sulfonyl]aziridine-2-carboxylate.

The invention also relates to the method for the preparation of N,N-disubstituted aromatic sulphonamides derivatives of formula (I), wherein solution of appropriate aziridine derivative, selected from group, consisting of-methyl-aziridin-2-carboxylate, 2-cyano-aziridine, aziridine-2-carboxamide, aziridine-2-carboxaldehyde, aziridine-2-methylketone and aziridine-2-N,N-dialkylcarboxamide racemates or its enantiomers is treated with appropriate sufonylchloride, selected from group of aryl-sulfonylchloride, wherein aryl- is selected from group of substituents, consisting of:

mono, di- and tri-substituted phenyl group of formula (III):

(III)

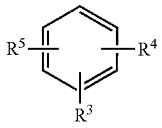

wherein $R^3$, $R^4$ and $R^5$ independently represent H, linear alkyl group $C_1$-$C_{12}$, O-alkyl $C_1$-$C_4$, branched alkyl $C_3$-$C_4$, cycloalkyl, phenyl, $NO_2$, halogen (Cl, F), trifluoromethyl, lower $C_1$-$C_4$ alkoxy, lower $C_1$-$C_4$ dialkylamino, lower $C_1$-$C_4$ acylamino;

or wherein Aryl- represents unsubstituted-, mono- and di-substituted-α-, β- and γ-naphthyl-group of formula IV:

(IV)

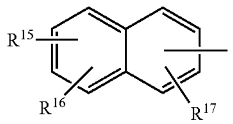

wherein $R^{15}$, $R^{16}$ and $R^{17}$ independently represent: H, lower alkyl $C_1$-$C_4$, Cl, O-alkyl $C_1$-$C_4$, —CHO or $NR^{18}R^{19}$, wherein $R^{18}$ and $R^{19}$ independently represent H, lower alkyl $C_1$-$C_4$, or wherein Aryl- represents pyridin-3-yl group of formula V:

(V)

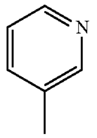

or 2-oxochromen-6-yl group of formula VI:

(VI)

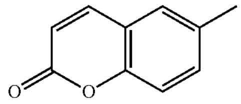

or 2-oxo-1H-quinolin-6-yl group of formula VII:

(VII)

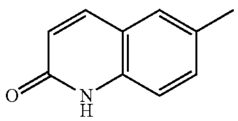

The invention also relates to N,N-disubstituted aromatic sulphonamides of formula (I) in form of racemates or enantiomers that inhibits PDI A3:

(I)

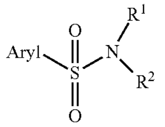

or a pharmaceutically acceptable salt and/or prodrug, wherein:

$R^1$ and $R^2$ taken together represent group of substituents consisting of formula (II)

(II)

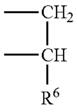

wherein $R^6$ represents CN, $CONR^7R^8$, $COOR^9$, $COO^-$ $Met^+$, $COR^{10}$,

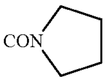 , 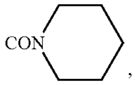 , 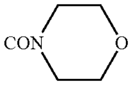

wherein $R^7$ and $R^8$ independently represent H or lower alkyl $C_1$-$C_4$, and $R^9$ and $R^{10}$ independently represent lower alkyl $C_1$-$C_4$, $Met^+$ represents an alkali metal cation $Li^+$, $Na^+$ or $K^+$, Aryl- represents mono, di- and tri-substituted phenyl group of formula (III):

(III)

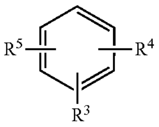

wherein $R^3$, $R^4$ and $R^5$ independently represent H, linear alkyl group $C_1$-$C_{12}$, O-alkyl $C_1$-$C_4$, branched alkyl $C_3$-$C_4$, cycloalkyl, phenyl, $NO_2$, halogen (Cl, F), trifluoromethyl, lower $C_1$-$C_4$ alkoxy, lower $C_1$-$C_4$ dialkylamino, lower $C_1$-$C_4$ acylamino group;

or Aryl represents unsubstituted-, mono- and di-substituted-α-, β- and γ-naphthyl-group of formula IV:

(IV)

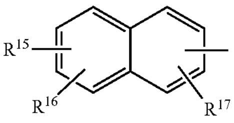

wherein $R^5$, $R^{16}$ and $R^{17}$ independently represent H, lower alkyl $C_1$-$C_4$, Cl, O-alkyl $C_1$-$C_4$, —CHO and $NR^{18}R^{19}$, where $R^{18}$ and $R^{19}$ are H or lower alkyl $C_1$-$C_4$;

or Aryl represents pyridin-3-yl group of formula V:

(V)

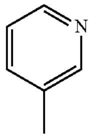

or 2-oxochromen-6-yl group of formula VI:

(VI)

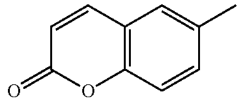

or 2-oxo-1H-quinolin-6-yl group of formula VII:

(VII)

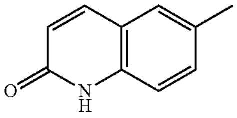

for use as a medicament.

Preferably, these compounds are for use in treatment and prevention of excessive platelet activation and thrombosis, in particular any disease from the list: disease or condition is thrombosis, thrombotic diseases, in particular the thrombotic disease is acute myocardial infarction, stable angina, unstable angina, aortocoronary bypass surgery, acute occlusion following coronary angioplasty and/or stent placement, transient ischemic attacks, cerebrovascular disease, peripheral vascular disease, placental insufficiency, prosthetic heart valves, atrial fibrillation, anticoagulation of tubing, deep vein thrombosis or pulmonary embolism and other pathologies linked with excessive activation of platelets and thrombosis including cancer-related thrombosis.

Also preferably, these compounds are for use as in treatment and prevention of cancer in particular any disease from the list: gastrointestinal cancer, colorectal cancer, colon cancer, liver cancer, hepatocellular carcinoma, pancreatic cancer, biliary tract cancer, stomach cancer, genitourinary cancer, bladder cancer, testicular cancer, cervical cancer, malignant mesothelioma, osteogenic sarcoma, esophageal cancer, laryngeal cancer, prostate cancer, hormone-refractory prostate cancer, lung cancer, small cell lung cancer, non-small cell lung cancer, breast cancer, triple-negative breast cancer, breast cancer having a BRCA1 and/or BRCA2 gene mutation, hematological cancer, leukemia, acute lymphoblastic leukemia, acute myeloid leukemia, chronic lymphocytic leukemia, chronic myeloid leukemia, lymphoma, Hodgkin lymphoma, non-Hodgkin lymphoma, follicular lymphoma, diffuse large B-cell lymphoma, ovarian cancer, brain cancer, neuroblastoma, Ewing's sarcoma, kidney cancer, epidermoid cancer, skin cancer, melanoma, head and/or neck cancer, head and neck squamous cell carcinoma, and mouth cancer.

The invention has been described in embodiments and figures non-limiting of the scope of protection, where:

FIG. 5*a* i 5*b;*

EXAMPLE 1. CHEMICAL SYNTHESIS

Figure 1:
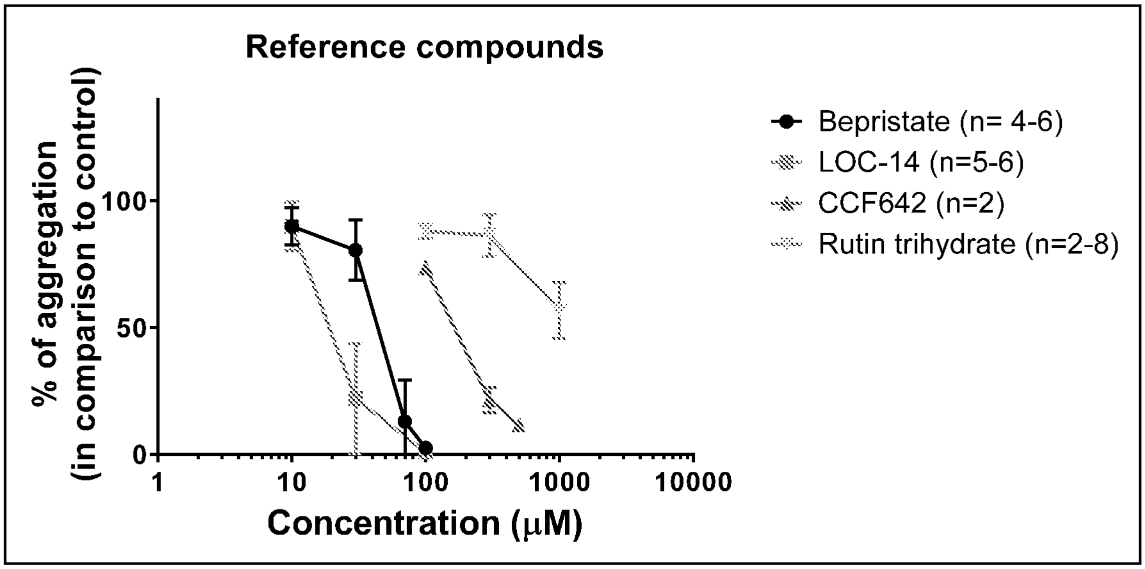
FIG. 1 shows inhibition of aggregation of human platelets by reference PDI inhibitors.

It is described below the general method for the preparation of the aziridine aromatic N-sulphonamides of formula (I).

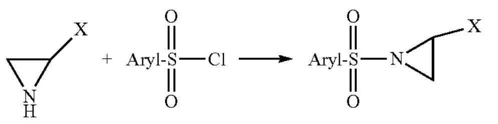

X=COOAlkyl, $CONH_2$, CONHAlkyl, $CONAlkyl_2$, CN, CHO, COAlkyl,

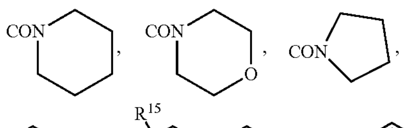

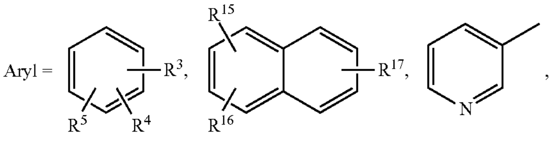

-continued

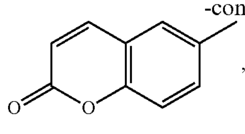

,

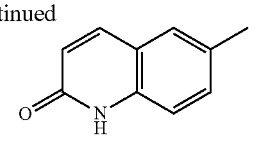

wherein $R^3$, $R^4$ and $R^5$ are: H, linear alkyl group $C_1$-$C_{12}$, O-alkyl $C_1$-$C_4$, branched alkyl $C_3$-$C_4$, cycloalkyl, phenyl, $NO_2$, halogen (Cl, F), trifluoromethyl, lower $C_1$-$C_4$ alkoxy, lower $C_1$-$C_4$ dialkylamino, lower $C_1$-$C_4$ acylamino; and $R^5$, $R^{16}$, $R^{17}$ are: H, lower alkyl $C_1$-$C_4$, Cl, O-alkyl $C_1$-$C_4$, —CHO and $NR^{18}R^{19}$, where $R^{18}$ and $R^{19}$ are H or lower alkyl $C_1$-$C_4$ Aromatic or heteroaromatic sulphonic acid chloride (1 mmol) was added with stirring to the solution of the appropriated aziridine (1.1 mmol) and $K_2CO_3$ (2 mmol) in the mixture of 1 ml $CHCl_3$+1 ml water. The mixture was stirred for 24 h. at room temperature. Product was extracted with $CHCl_3$, and the solution dried over $MgSO_4$. The solvent was evaporated. The product was purified by chromatography (silica gel, petroleum ether/ethyl acetate 4:1=>1:2) to give corresponding aziridine aromatic N-sulfonamide. 1-(p-Tolylsulfonyl)aziridine-2-carbonitrile (C-3314) was prepared as described by Nadir, U. K. and Singh, A. Synthetic Communications, 34(7), 1337-1347; 2004. 1-(p-Tolylsulfonyl)aziridine-2-carbaldehyde (C-3262) was prepared as described by Lapinsky, D. J. and Bergmeier, S. C. Tetrahedron Letters, 42(49), 8583-8586; 2001. 1-(4-Butylphenyl) sulfonylaziridine-2-carbaldehyde (C-3273) was prepared using the same method. 1-[1-(p-Tolylsulfonyl)aziridin-2-yl] ethanone (C-3263) was prepared as described by Smith, A. B., and Kim, D.-S. Journal of Organic Chemistry, 71(7), 2547-2557; 2006. 1-[1-(4-Butylphenyl)sulfonylaziridin-2-yl]ethanone (C-3272) was prepared using the same method. Methyl (2S)-1-(p-tolylsulfonyl)aziridine-2-carboxylate (C-3535) was prepared as described by Qian, G.; Bai, M.; Gao, S.; Chen, H.; Zhou, S.; Cheng, H-G.; Yan, W.; Zhou, Q. Angewandte Chemie, International Edition (2018), 57(34), 10980-10984. Methyl (2R)-1-(p-tolylsulfonyl)aziridine-2-carboxylate (C-3539) was prepared as described by Smith, A. B. and Kim, D-S. Journal of Organic Chemistry (2006), 71(7), 2547-2557. Methyl (2S)-1-[[6-(dimethylamino)-1-naphthyl]sulfonyl]aziridine-2-carboxylate (C-3548) and methyl (2R)-1-[[6-(dimethylamino)-1-naphthyl]sulfonyl]aziridine-2-carboxylate (C-3570) were prepared using methodology as described by Smith, A. B. and Kim, D-S. Journal of Organic Chemistry (2006), 71(7), 2547-2557.

Lithium 1-tosylaziridine-2-carboxylate (C-3612) was prepared as described by Baldwin, J. E.; Spivey, A. C.; Schofield, C. J.; Sweeney, J. B. Tetrahedron, 49(28), 6309-30; 1993

Synthesis of 6-(dimethylamino)-5-formylnaphthalene-1-sulfonyl chloride

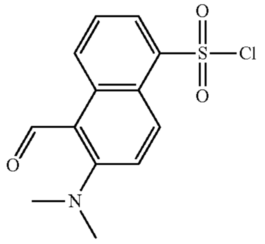 [SMILES: CN(C)c1ccc2c(S(=O)(=O)Cl)cccc2c1C=O]

Into a 50 mL round-bottom flask, was placed 6-(dimethylamino)naphthalene-1-sulfonic acid (1.0 g, 3.98 mmol). To this was added $CH_2Cl_2$ (20 mL). To the mixture was added DMF (0.4 mL). To the above was added dropwise oxalyl dichloride (2.0 g, 15.74 mmol). The resulting solution was allowed to react with stirring for 24 h at room temperature. The reaction mixture was then quenched by the adding 50 mL of ice/salt. The resulting solution was extracted twice with 10 mL of $CH_2Cl_2$ and the organic layers combined and dried over $Na_2SO_4$. Solvent was evaporated under vacuum. The resulted 6-(dimethylamino)-5-formylnaphthalene-1-sulfonyl chloride (0.83 g 70%) was used on the next stage without additional purification. $^1$H-NMR spectrum (400 MHz): ($CDCl_3$, HMDSO) δ: 10.30 (s, 1H), 9.55 (dt, J=8.7, 1.0 Hz, 1H), 8.87 (dd, J=9.7, 0.9 Hz, 1H), 8.18 (dd, J=7.6, 1.1 Hz, 1H), 7.66 (dd, J=8.7, 7.6 Hz, 1H), 7.60 (d, J=9.7 Hz, 1H), 3.22 (s, 6H).

The same method was used for the preparation of 6-(dimethylamino)-5-formylnaphthalene-2-sulfonyl chloride.

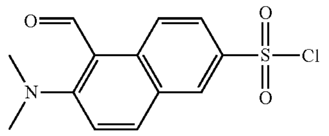 [SMILES: CN(C)c1ccc2cc(S(=O)(=O)Cl)ccc2c1C=O]

$^1$H-NMR spectrum (400 MHz): ($CDCl_3$, HMDSO) δ: 10.26 (s, 1H), 8.91 (d, J=9.1 Hz, 1H), 8.11 (d, J=9.1 Hz, 1H), 8.11 (m, 1H), 7.75 (dd, J=9.1, 2.0 Hz, 1H), 7.51 (d, J=9.1 Hz, 1H), 7.41 (d, J=9.1 Hz, 1H), 3.13 (s, 6H).

Synthesis of 5-chloro-6-(methylamino)naphthalene-2-sulfonyl chloride

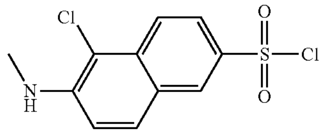 [SMILES: CNc1ccc2cc(S(=O)(=O)Cl)ccc2c1Cl]

To a suspension of 6-(dimethylamino)naphthalene-2-sulfonic acid (1.0 g, 3.98 mmol). in $POCl_3$ (5 mL) was slowly added $PCl_5$ (3.7 g, 17.8 mmol). The resulting mixture was heated at 50° C. for 5 h before it was allowed to cool to room temperature and poured onto crushed ice. The aqueous mixture was stirred vigorously at 0° C. for 40 min. Product was extracted twice with 40 mL of $CH_2Cl_2$ and the organic layers combined and dried over $Na_2SO_4$. Solvent was evaporated under vacuum. The resulted 5-chloro-6-(methylamino)naphthalene-2-sulfonyl chloride was purified by chromatography (silica gel, petroleum ether/ethyl acetate 4:1). Yield 0.35 g (30%). $^1$H-NMR spectrum (400 MHz): ($CDCl_3$, HMDSO) δ: 8.24 (d, J=2.0 Hz, 1H), 8.15 (dt, J=9.2, 0.6 Hz, 1H), 7.95 (dd, J=9.2, 2.0 Hz, 1H), 7.86 (d, J=9.0 Hz, 1H), 7.22 (d, J=9.0 Hz, 1H), 3.11 (s, 3H).

TABLE 1

| | |
|---|---|
| C-3161 | Methyl 1-(p-tolylsulfonyl)aziridine-2-carboxylate<br>Molecular formula: $C_{11}H_{13}NO_4S$; Molecular weight: 255.29; Melting point: 56-58° C.; $^1$H-NMR spectrum (400 MHz): ($CDCl_3$, HMDSO) δ: 7.84 (d, J = 8.3 Hz, 2H), 7.35 (d, J = 8.3 Hz, 2H), 3.74 (s, 3H), 3.34 (dd, J = 7.1, 4.1 Hz, 1H), 2.76 (d, J = 7.1 Hz, 1H), 2.56 (d, J = 4.1 Hz, 1H), 2.45 (s, 3H); $^{13}$C-NMR spectrum (100 MHz): ($CDCl_3$, HMDSO) δ: 167.2, 145.2, 134.0, 129.9, 128.2, 52.9, 35.7, 32.0, 21.7; LCMS $ESI^-$ (m/z): 254.2 $[M - H]^-$, LCMS purity 100.00% |
| C-3212 | Methyl 1-(4-nitrophenyl)sulfonylaziridine-2-carboxylate<br>Molecular formula: $C_{10}H_{10}N_2O_6S$; Molecular weight: 286.26; Melting point: 106-108° C.; $^1$H-NMR spectrum (400 MHz): ($CDCl_3$, HMDSO) δ: 8.41 (d, J = 9.0 Hz, 2H), 8.18 (d, J = 9.0 Hz, 2H), 3.76 (s, 3H), 3.46 (dd, J = 7.1, 4.3 Hz, 1H), 2.89 (d, J = 7.1 Hz, 1H), 2.66 (d, J = 4.3 Hz, 1H); $^{13}$C-NMR spectrum (100 MHz): ($CDCl_3$, HMDSO) δ: 166.6, 150.9, 142.9, 129.5, 124.5, 53.1, 35.2, 32.5; LCMS $ESI^-$ (m/z): 285.1 $[M - H]^-$, LCMS purity 100.00% |
| C-3216 | 1-(4-Nitrophenyl)sulfonylaziridine-2-carboxamide<br>Molecular formula: $C_9H_9N_3O_5S$; Molecular weight: 271.25; Melting point: 179-181° C.; $^1$H-NMR spectrum (400 MHz): (DMSO-d6, HMDSO) δ: 8.47 (d, J = 8.9 Hz, 2H), 8.24 (d, J = 8.8 Hz, 2H), 7.87 (br s, 1H), 7.47 (br s, 1H), 3.39 (dd, J = 7.2, 4.5 Hz, 1H), 2.79 (d, J = 7.2 Hz, 1H), 2.58 (d, J = 4.5 Hz, 1H); $^{13}$C-NMR spectrum (100 MHz): (DMSO-d6, HMDSO) δ: 166.5, 151.2, 142.6, 130.0, 125.3, 37.6, 32.2; LCMS $ESI^+$ (m/z): 271.9 $[M + H]^+$; Impurities: 3.67% (210 nm); 2.24% (254 nm) |
| C-3218 | 1-(4-Aminophenyl)sulfonylaziridine-2-carboxamide<br>Molecular formula: $C_9H_{11}N_3O_3S$; Molecular weight: 241.27; Melting point: 139-141° C.; $^1$H-NMR spectrum (400 MHz): ($CDCl_3$, HMDSO) δ: 7.72 (s, 1H), 7.50 (d, J = 8.7 Hz, 2H), 7.34 (s, 1H), 6.65 (d, J = 8.7 Hz, 2H), 6.25 (s, 2H), 3.01 (dd, J = 7.1, 4.1 Hz, 1H), 2.41 (d, J = 7.1 Hz, 1H), 2.35 (d, J = 4.1 Hz, 1H); $^{13}$C-NMR spectrum (100 MHz): (DMSO-$d_6$, HMDSO) δ: 167.5, 154.6, 130.5, 120.5, 113.2, 36.8, 31.2; LCMS $ESI^-$ (m/z): 242.2 $[M - H]^-$, LCMS purity 100.00% |
| C-3220 | 1-(p-Tolylsulfonyl)aziridine-2-carboxamide<br>Molecular formula: $C_{10}H_{12}N_2O_3S$; Molecular weight: 240.28; Melting point: 118-120° C.; $^1$H-NMR spectrum (400 MHz): ($CDCl_3$, HMDSO) δ: 7.82 (d, J = 8.2 Hz, 2H), 7.37 (d, J = 8.2 Hz, 2H), 6.11 (s, 1H), 5.76 (s, 1H), 3.23 (dd, J = 7.7, 4.2 Hz, 1H), 2.80 (d, J = 7.7 Hz, 1H), 2.48 (s, 3H), 2.43 (d, J = 4.2 Hz, 1H); $^{13}$C-NMR spectrum (100 MHz): ($CDCl_3$, HMDSO) δ: 168.3, 145.6, 133.4, 130.0, 128.2, 37.6, 33.1, 21.7; LCMS $ESI^-$ (m/z): 241.2 $[M - H]^-$, LCMS purity 100.00% |
| C-3251 | Methyl 1-(benzenesulfonyl)aziridine-2-carboxylate<br>Molecular formula: $C_{10}H_{11}NO_4S$; Molecular weight: 241.26; Melting point: oil; $^1$H-NMR spectrum (400 MHz): ($CDCl_3$) δ: 7.00-8.94 (m, 2H), 7.71-7.64 (m, 1H), 7.60-7.53 (m, 2H), 3.74 (s, 3H), 3.37 (dd, J = 7.1, 4.1 Hz, 1H), 2.79 (d, J = 7.1 Hz, 1H), 2.58 (d, J = 4.1 Hz, 1H); $^{13}$C-NMR spectrum (100 MHz): ($CDCl_3$) δ: 167.3, 137.2, 134.3, 129.4, 128.3, 53.1, 35.9, 32.3; LCMS $ESI^+$ (m/z): 242.1 $[M + H]^+$, LCMS purity 100.00% |

TABLE 1-continued

| | |
|---|---|
| C-3256 | Methyl 1-[4-(trifluoromethyl)phenyl]sulfonylaziridine-2-carboxylate<br>Molecular formula: $C_{11}H_{10}F_3NO_4S$; Molecular weight: 309.26; Melting point: 68-70° C.; $^1$H-NMR spectrum (400 MHz): ($CDCl_3$, HMDSO) δ: 8.12 (d, J = 8.4 Hz, 2H), 7.84 (d, J = 8.4 Hz, 2H), 3.76 (s, 3H), 3.43 (dd, J = 7.1, 4.2 Hz, 1H), 2.85 (dd, J = 7.1, 0.9 Hz, 1H), 2.63 (dd, J = 4.2, 0.9 Hz, 1H); $^{13}$C-NMR spectrum (100 MHz): ($CDCl_3$, HMDSO) δ: 166.8, 140.8, 135.7 (q, J = 33.1 Hz), 128.7, 126.4 (q, J = 3.7 Hz), 123.0 (q, J = 273.4 Hz), 53.0, 36.0, 32.3; LCMS ESI$^-$ (m/z): 308.2 $[M - H]^-$, LCMS purity 100.00% |
| C-3257 | Methyl 1-(4-butylphenyl)sulfonylaziridine-2-carboxylate<br>Molecular formula: $C_{14}H_{19}NO_4S$; Molecular weight: 297.37; Melting point: oil; $^1$H-NMR spectrum (400 MHz): ($CDCl_3$, HMDSO) δ: 7.86 (d, J = 8.4 Hz, 2H), 7.36 (d, J = 8.4 Hz, 2H), 3.74 (s, 3H), 3.35 (dd, J = 7.1, 4.1 Hz, 1H), 2.76 (d, J = 7.1 Hz, 1H), 2.70 (t, J = 7.7 Hz, 2H), 2.56 (d, J = 4.1 Hz, 1H), 1.58-1.67 (m, 2H), 1.36 (sextet, J = 7.5 Hz, 2H), 0.94 (d, J = 7.4 Hz, 3H); $^{13}$C-NMR spectrum (100 MHz): ($CDCl_3$, HMDSO) δ: 167.3, 150.1, 134.1, 129.2, 128.2, 52.9, 35.6, 35.6, 32.1, 32.1, 22.2, 13.8; LCMS ESI$^+$ (m/z): 298.2 $[M + H]^+$, LCMS purity 100% |
| C-3262 | 1-(p-Tolylsulfonyl)aziridine-2-carbaldehyde<br>Molecular formula: $C_{10}H_{11}NO_4S$; Molecular weight: 225.26; Melting point: oil; $^1$H-NMR spectrum (400 MHz): ($CDCl_3$, HMDSO) δ: 8.95 (d, J = 5.9 Hz, 1H), 7.84 (d, J = 8.3 Hz, 2H), 7.38 (d, J = 8.3 Hz, 2H), 3.27 (ddd, J = 7.4, 5.9, 4.0 Hz, 1H), 2.93 (d, J = 7.4 Hz, 1H), 2.58 (d, J = 4.0 Hz, 1H), 2.47 (s, 3H); $^{13}$C-NMR spectrum (100 MHz): ($CDCl_3$, HMDSO) δ: 194.3, 145.6, 133.7, 130.0, 128.2, 41.9, 30.1, 21.7; LCMS ESI$^+$ (m/z): 226.2 $[M + H]^+$, LCMS purity 94.70% |
| C-3263 | 1-[1-(p-Tolylsulfonyl)aziridin-2-yl]ethanone<br>Molecular formula: $C_{11}H_{13}NO_3S$; Molecular weight: 239.29; Melting point: 90-92° C.; $^1$H-NMR spectrum (400 MHz): ($CDCl_3$, HMDSO) δ: 7.84 (d, J = 8.3 Hz, 2H), 7.37 (d, J = 8.3 Hz, 2H), 3.29 (dd, J = 7.4, 4.1 Hz, 1H), 2.80 (d, J = 7.1 Hz, 1H), 2.49 (d, J = 4.1 Hz, 1H), 2.46 (s, 3H), 2.07 (s, 3H); $^{13}$C-NMR spectrum (100 MHz): ($CDCl_3$, HMDSO) δ: 201.4, 145.3, 133.9, 129.9, 128.1, 41.9, 31.8, 25.9, 21.7; LCMS ESI+ (m/z): 240.2 [M + H]+. LCMS purity 100%; Elemental analysis: Found [%]: C 55.07, H 5.35, N 5.74; Calculated [%]: C 55.21, H 5.48, N 5.85 |
| C-3270 | Methyl 1-(4-dodecylphenyl)sulfonylaziridine-2-carboxylate<br>Molecular formula: $C_{22}H_{35}NO_4S$; Molecular weight: 409.58; Melting point: oil; $^1$H-NMR spectrum (400 MHz): ($CDCl_3$, HMDSO) δ: 7.86 (d, J = 8.4 Hz, 2H), 7.35 (d, J = 8.4 Hz, 2H), 3.74 (s, 3H), 3.36 (dd, J = 7.1, 4.1 Hz, 1H), 2.77 (d, J = 7.1 Hz, 1H), 2.69 (t, J = 7.7 Hz, 2H), 2.56 (d, J = 4.1 Hz, 1H), 1.63 (quintet, J = 7.5 Hz, 2H), 1.20-1.38 (m, 18H), 0.87 (d, J = 6.9 Hz, 3H); $^{13}$C-NMR spectrum (100 MHz): ($CDCl_3$, HMDSO) δ: 167.3, 150.2, 134.1, 129.2, 128.2, 52.9, 36.0, 35.6, 32.1, 31.9, 29.6, 29.5, 29.4, 29.3, 29.2, 22.7, 14.1; LCMS ESI$^+$ (m/z): 410.4 $[M + H]^+$, LCMS purity 100.00% |
| C-3271 | Methyl 1-(4-butoxyphenyl)sulfonylaziridine-2-carboxylate<br>Molecular formula: $C_{14}H_{19}NO_5S$; Molecular weight: 313.37; Melting point: oil; $^1$H-NMR spectrum (400 MHz): ($CDCl_3$, HMDSO) δ: 7.87 (d, J = 8.4 Hz, 2H), 7.00 (d, J = 8.4 Hz, 2H), 4.04 (t, J = 6.5 Hz, 2H), 3.74 (s, 3H), 3.32 (dd, J = 7.1, 4.1 Hz, 1H), 2.74 (d, J = 7.1 Hz, 1H), 2.55 (d, J = 4.1 Hz, 1H), 1.80 (quintet, J = 6.7 Hz, 2H), 1.50 (sextet, J = 7.5 Hz, 2H), 0.99 (t, J = 7.4 Hz, 3H); $^{13}$C-NMR spectrum (100 MHz): ($CDCl_3$, HMDSO) δ: 167.3, 163.7, 130.4, 127.9, 114.9, 68.3, 52.8, 35.6, 32.0, 30.9, 19.1, 13.7; LCMS ESI$^+$ (m/z): 314.3 $[M + H]^+$; LCMS purity 93.03% |
| C-3272 | 1-[1-(4-Butylphenyl)sulfonylaziridin-2-yl]ethanone<br>Molecular formula: $C_{14}H_{19}NO_3S$; Molecular weight: 281.37; Melting point: oil; $^1$H-NMR spectrum (400 MHz): ($CDCl_3$, HMDSO) δ: 7.84 (d, J = 8.4 Hz, 2H), 7.36 (d, J = 8.3 Hz, 2H), 3.29 (dd, J = 7.4, 4.1 Hz, 1H), 2.70 (t, J = 7.7 Hz, 2H), 2.79 (d, J = 7.4 Hz, 1H), 2.49 (d, J = 4.1 Hz, 1H), 2.46 (s, 3H), 2.07 (s, 3H), 1.57-1.67 (m, 2H), 1.36 (sextet, J = 7.5 Hz, 2H), 0.93 (t, J = 7.4 Hz, 3H); $^{13}$C-NMR spectrum (100 MHz): ($CDCl_3$, HMDSO) δ: 201.5, 150.2, 134.0, 129.3, 128.2, 41.9, 35.6, 33.0, 31.9, 25.9, 22.2, 13.8; LCMS ESI+ (m/z): 282.3 $[M + H]^+$, LCMS purity 96.65% |
| C-3273 | 1-(4-Butylphenyl)sulfonylaziridine-2-carbaldehyde<br>Molecular formula: $C_{13}H_{17}NO_3S$; Molecular weight: 267.34; Melting point: oil; $^1$H-NMR spectrum (400 MHz): ($CDCl_3$, HMDSO) δ: 8.96 (d, J = 5.8 Hz, 1H), 7.85 (d, J = 8.4 Hz, 2H), 7.38 (d, J = 8.3 Hz, 2H), 3.28 (ddd, J = 7.4, 5.8, 4.0 Hz, 1H), 2.93 (d, J = 7.4 Hz, 1H), 2.71 (t, J = 7.8 Hz, 2H), 2.58 (d, J = 4.0 Hz, 1H), 1.57-1.68 (m, 2H), 1.37 (sextet, J = 7.5 Hz, 2H), 0.94 (t, J = 7.5 Hz, 3H); $^{13}$C-NMR spectrum (100 MHz): ($CDCl_3$, HMDSO) δ: 194.3, 150.4, 133.8, 129.4, 128.2, 41.8, 35.6, 33.0, 30.1, 22.2, 13.8; LCMS ESI$^+$ (m/z): 268.4 $[M + H]^+$, LCMS purity 100.00% |
| C-3281 | Methyl 1-(4-pentylphenyl)sulfonylaziridine-2-carboxylate<br>Molecular formula: $C_{15}H_{21}NO_4S$; Molecular weight: 311.40; Melting point: oil; $^1$H-NMR spectrum (400 MHz): ($CDCl_3$, HMDSO) δ: ($CDCl_3$, HMDSO) δ: 7.86 (d, J = 8.4 Hz, 2H), 7.39 (d, J = 8.4 Hz, 2H), 3.74 (s, 3H), 3.36 (dd, J = 7.1, 4.1 Hz, 1H), 2.77 (d, J = 7.1 Hz, 1H), 2.69 (t, J = 7.8 Hz, 2H), 2.56 (d, J = 4.1 Hz, 1H), 1.64 (quintet, J = 7.5 Hz, 2H), 1.27-1.40 (m, 4H), 0.90 (t, J = 7.0 Hz, 3H); $^{13}$C-NMR spectrum (100 MHz): ($CDCl_3$, HMDSO) δ: 167.2, 150.1, 134.1, 129.2, 128.2, 52.8, 35.8, 35.6, 32.1, 31.3, 30.6, 22.4, 13.9; LCMS ESI$^+$ (m/z): 312.4 $[M + H]^+$, LCMS purity 100.00% |
| C-3287 | Methyl 1-(4-hexylphenyl)sulfonylaziridine-2-calboxylate<br>Molecular formula: $C_{16}H_{23}NO_4S$; Molecular weight: 325.42; Melting point: oil; $^1$H-NMR spectrum (400 MHz): ($CDCl_3$) δ: 7.88-7.83 (m, 2H), 7.38-7.32 (m, 2H), 3.74 (s, 3H), 3.35 (dd, J = 7.1, 4.1 Hz, 1H), 2.76 (d, J = 7.1 Hz, 1H), 2.73-2.65 (m, 2H), 2.56 (d, J = 4.1 Hz, 1H), 1.68-1.58 (m, 2H), 1.38-1.24 (m, 6H), 0.92-0.84 (m, 3H); $^{13}$C-NMR spectrum (100 MHz): ($CDCl_3$) δ: 167.4, 150.3, 134.3, 129.4, 128.4, 53.0, 36.1, 35.8, 32.2, 31.7, 31.1, 29.0, 22.7, 14.2; LCMS ESI+ (m/z): 326.2 [M + H]+. LCMS purity 99.43% |
| C-3288 | Methyl 1-(4-heptylphenyl)sulfonylaziridine-2-carboxylate<br>Molecular formula: $C_{17}H_{25}NO_4S$; Molecular weight: 339.45; Melting point: oil; $^1$H-NMR spectrum (400 MHz): ($CDCl_3$, HMDSO) δ: 7.86 (d, J = 8.5 Hz, 2H), 7.36 (d, J = 8.5 Hz, 2H), 3.74 (s, 3H), 3.36 (dd, J = 7.1, 4.1 Hz, 1H), 2.77 (d, J = 7.1 Hz, 1H), 2.69 (t, J = 7.7 Hz, 2H), 2.56 (d, J = 4.1 Hz, 1H), 1.63 (quintet, J = 7.5 Hz, 2H), 1.22-1.37 (m, 8H), 0.88 (t, J = 7.1 Hz, 3H); $^{13}$C-NMR spectrum (100 MHz): ($CDCl_3$, HMDSO) δ: 167.3, 150.1, 134.1, 129.2, 128.2, 52.9, 35.9, 35.6, 32.1, 31.7, 31.0, 29.1, 29.0, 22.6, 14.0; LCMS ESI$^+$ (m/z): 340.4 $[M + H]^+$, LCMS purity 100.00% |

TABLE 1-continued

| | |
|---|---|
| C-3290 | Methyl 1-(4-tert-butylphenyl)sulfonylaziridine-2-carboxylate<br>Molecular formula: $C_{14}H_{19}NO_4S$; Molecular weight: 297.37; Melting point: oil; $^1$H-NMR spectrum (400 MHz): ($CDCl_3$, HMDSO) δ: 7.88 (d, J = 8.6 Hz, 2H), 7.57 (d, J = 8.6 Hz, 2H), 3.74 (s, 3H), 3.37 (dd, J = 7.1, 4.1 Hz, 1H), 2.76 (d, J = 7.1 Hz, 1H), 2.56 (d, J = 4.1 Hz, 1H), 1.35 (s, 9H); $^{13}$C-NMR spectrum (100 MHz): ($CDCl_3$, HMDSO) δ: 167.3, 158.1, 133.9, 128.0, 126.3, 52.9, 35.6, 35.3, 32.1, 31.0; LCMS ESI$^+$ (m/z): 398.3 $[M + H]^+$, LCMS purity 100.00% |
| C-3291 | Methyl 1-(4-phenylphenyl)sulfonylaziridine-2-carboxylate<br>Molecular formula: $C_{16}H_{15}NO_4S$; Molecular weight: 317.36; Melting point: 90-92° C.; $^1$H-NMR spectrum (400 MHz): ($CDCl_3$, HMDSO) δ: 8.03 (d, J = 8.8 Hz, 2H), 7.77 (d, J = 8.8 Hz, 2H), 7.60-7.62 (m, 2H), 7.41-7.52 (m, 3H), 3.76 (s, 3H), 3.41 (dd, J = 7.1, 4.1 Hz, 1H), 2.82 (d, J = 7.1 Hz, 1H), 2.61 (d, J = 4.1 Hz, 1H); $^{13}$C-NMR spectrum (100 MHz): ($CDCl_3$, HMDSO) δ: 167.2, 147.1, 139.0, 135.5, 129.1, 128.7, 128.7, 127.9, 127.4, 52.9, 35.7, 32.1; LCMS ESI$^+$ (m/z): 318.3 $[M + H]^+$, LCMS purity 100.00% |
| C-3292 | Methyl 1-(2-naphthylsulfonyl)aziridine-2-carboxylate<br>Molecular formula: $C_{14}H_{13}NO_4S$; Molecular weight: 291.32; Melting point: oil; $^1$H-NMR spectrum (400 MHz): ($CDCl_3$, HMDSO) δ: 8.52-8.54 (m, 1H), 7.99-8.03 (m, 2H), 7.93-7.97 (m, 2H), 7.67-7.72 (m, 1H), 7.62-7.67 (m, 1H), 3.73 (s, 3H), 3.44 (dd, J = 7.1, 4.1 Hz, 1H), 2.85 (d, J = 7.1 Hz, 1H), 2.60 (d, J = 4.1 Hz, 1H); $^{13}$C-NMR spectrum (100 MHz): ($CDCl_3$, HMDSO) δ: 167.1, 135.5, 133.9, 132.0, 129.9, 129.6, 129.5, 129.5, 128.0, 127.8, 122.8, 52.9, 35.8, 32.1; LCMS ESI+ (m/z): 292.3 [M + H]+, LCMS purity 97.48% |
| C-3294 | Methyl 1-(4-methoxyphenyl)sulfonylaziridine-2-carboxylate<br>Molecular formula: $C_{11}H_{13}NO_5S$; Molecular weight: 271.29; Melting point: 73-75° C.; $^1$H-NMR spectrum (400 MHz): ($CDCl_3$, HMDSO) δ: 7.89 (d, J = 9.1 Hz, 2H), 7.01 (d, J = 9.1 Hz, 2H), 3.89 (s, 3H), 3.74 (s, 3H), 3.32 (dd, J = 7.1, 4.1 Hz, 1H), 2.75 (d, J = 7.1 Hz, 1H), 2.55 (d, J = 4.1 Hz, 1H); $^{13}$C-NMR spectrum (100 MHz): ($CDCl_3$, HMDSO) δ: 167.3, 164.1, 130.4, 128.3, 114.5, 55.7, 52.8, 35.7, 32.0; LCMS ESI+ (m/z): 272.3 [M + H]+, LCMS purity 100% |
| C-3295 | Methyl 1-(4-isopropylphenyl)sulfonylaziridine-2-carboxylate<br>Molecular formula: $C_{13}H_{17}NO_4S$; Molecular weight: 283.34; Melting point: oil; $^1$H-NMR spectrum (400 MHz): ($CDCl_3$, HMDSO) δ: 7.88 (d, J = 8.6 Hz, 2H), 7.40 (d, J = 8.6 Hz, 2H), 3.75 (s, 3H), 3.36 (dd, J = 7.1, 4.1 Hz, 1H), 3.00 (septet, J = 6.9 Hz, 1H), 2.76 (d, J = 7.1 Hz, 1H), 2.56 (d, J = 4.1 Hz, 1H), 1.28 (d, J = 6.9 Hz, 6H); $^{13}$C-NMR spectrum (100 MHz): ($CDCl_3$, HMDSO) δ: 167.3, 155.9, 134.2, 128.3, 127.4, 52.8, 35.6, 34.2, 32.1, 23.5; LCMS ESI+ (m/z): 284.3 [M + H]+, LCMS purity 100% |
| C-3296 | Methyl 1-(4-chlorophenyl)sulfonylaziridine-2-carboxylate<br>Molecular formula: $C_{10}H_{10}ClNO_4S$; Molecular weight: 275.71; Melting point: oil; $^1$H-NMR spectrum (400 MHz): ($CDCl_3$, HMDSO) δ: 7.91 (d, J = 8.7 Hz, 2H), 7.55 (d, J = 8.7 Hz, 2H), 3.75 (s, 3H), 3.38 (dd, J = 7.1, 4.1 Hz, 1H), 2.80 (d, J = 7.1 Hz, 1H), 2.60 (d, J =4.1 Hz, 1H); $^{13}$C-NMR spectrum (100 MHz): ($CDCl_3$, HMDSO) δ: 166.9, 140.9, 135.6, 129.6, 129.6, 53.0, 35.9, 32.2; LCMS ESI$^+$ (m/z): 276.2 $[M + H]^+$, LCMS purity 100.00% |
| C-3297 | Methyl 1-(2-fluoro-4-methyl-phenyl)sulfonylaziridine-2-carboxylate<br>Molecular formula: $C_{13}H_{12}FNO_4S$; Molecular weight: 273.26; Melting point: oil; $^1$H-NMR spectrum (400 MHz): ($CDCl_3$, HMDSO) δ: 7.82 (dd, J = 8.0, 7.3 Hz, 1H), 7.10-7.13 (m, 1H), 7.04-7.08 (m, 1H), 3.77 (s, 3H), 3.50 (ddd, J = 7.1, 4.3, 0.9 Hz, 1H), 2.95 (dd, J = 7.1, 1.2 Hz, 1H), 2.66 (d, J = 4.3 Hz, 1H), 2.44 (s, 3H); $^{13}$C-NMR spectrum (100 MHz): ($CDCl_3$, HMDSO) δ: 167.2, 159.3 (d, J = 258.3 Hz,), 148.8 (d, J = 8.5 Hz,), 130.3, 125.2 (d, J = 3.0 Hz,), 122.4 (d, J = 14.5 Hz,), 117.8 (d, J = 20.9 Hz,),, 52.9, 35.9, 32.4, 21.6; LCMS ESI$^+$ (m/z): 274.3 $[M + H]^+$, LCMS purity 96.13% |
| C-3299 | Methyl 1-(4-propylphenyl)sulfonylaziridine-2-carboxylate<br>Molecular formula: $C_{13}H_{17}NO_4S$; Molecular weight: 283.34; Melting point: oil; $^1$H-NMR spectrum (400 MHz): ($CDCl_3$, HMDSO) δ: 7.86 (d, J = 8.5 Hz, 2H), 7.36 (d, J = 8.5 Hz, 2H), 3.74 (s, 3H), 3.36 (dd, J = 7.1, 4.1 Hz, 1H), 2.77 (d, J = 7.1 Hz, 1H), 2.68 (t, J = 7.6 Hz, 2H), 2.56 (d, J = 4.1 Hz, 1H), 1.68 (sextet, J = 7.5 Hz, 2H), 0.95 (t, J = 7.4 Hz, 3H); $^{13}$C-NMR spectrum (100 MHz): ($CDCl_3$, HMDSO) δ: ($CDCl_3$, HMDSO) δ: 167.2, 149.8, 134.2, 129.3, 128.2, 52.9, 37.9, 35.6, 32.1, 24.1, 13.6; LCMS ESI$^+$ (m/z): 284.3 $[M + H]^+$, LCMS purity 100.00% |
| C-3303 | Methyl 1-(m-tolylsulfonyl)aziridine-2-carboxylate<br>Molecular formula: $C_{11}H_{13}NO_4S$; Molecular weight: 255.29; Melting point: oil; $^1$H-NMR spectrum (400 MHz): ($CDCl_3$, HMDSO) δ: 7.88-7.80 (m, 1H), 7.74-7.77 (m, 1H), 7.46-7.50 (m, 1H), 7.42-7.46 (m, 1H), 3.74 (s, 3H), 3.37 (dd, J = 7.1, 4.1 Hz, 1H), 2.78 (d, J = 7.1 Hz, 1H), 2.57 (d, J = 4.1 Hz, 1H), 2.45 (s, 3H); $^{13}$C-NMR spectrum (100 MHz): ($CDCl_3$, HMDSO) δ: 167.2, 139.6, 136.8, 135.0, 129.1, 128.5, 125.2, 52.9, 35.6, 32.1, 24.3; LCMS ESI$^+$ (m/z): 256.2 $[M + H]^+$, LCMS purity 97.26% |
| C-3304 | Methyl 1-(4-propylphenyl)sulfonylaziridine-2-carboxylate<br>Molecular formula: $C_{13}H_{17}NO_4S$; Molecular weight: 283.34; Melting point:106-108° C.<br>$^1$H-NMR spectrum (400 MHz): ($CDCl_3$, HMDSO) δ: 6.98 (s, 2H), 3.74 (s, 3H), 3.34 (dd, J = 7.1, 4.1 Hz, 1H), 2.79 (d, J = 7.1 Hz, 1H), 2.69 (s, 6H), 2.51 (d, J = 4.1 Hz, 1H), 2.32 (s, 3H); $^{13}$C-NMR spectrum (100 MHz): ($CDCl_3$, HMDSO) δ: 167.5, 143.6, 140.4, 131.9, 131.7, 52.7, 34.7, 31.7, 22.9, 21.0<br>LCMS ESI+ (m/z): 284.3 [M + H]+, LCMS purity 100% |
| C-3305 | Methyl 1-[3-(trifluoromethyl)phenyl]sulfonylaziridine-2-carboxylate<br>Molecular formula: $C_{11}H_{10}F_3NO_4S$; Molecular weight: 309.26; Melting point: oil; $^1$H-NMR spectrum (400 MHz): ($CDCl_3$, HMDSO) δ: 8.23-8.26 (m, 1H), 8.16-8.20 (m, 1H), 7.92-7.96 (m, 1H), 7.71-7.77 (m, 1H), 3.76 (s, 3H), 3.45 (dd, J = 7.1, 4.2 Hz, 1H), 2.86 (dd, J = 7.1, 0.9 Hz, 1H), 2.64 (dd, J = 4.2, 0.9 Hz, 1H); $^{13}$C-NMR spectrum (100 MHz): ($CDCl_3$, HMDSO) δ: 166.8, 138.5, 132.0 (q, J = 34.1 Hz), 131.4, 130.8 (q, J = 3.6 Hz), 130.1, 125.2 (q, J = 3.8 Hz), 123.0 (q, J = 273.8 Hz), 53.0, 36.0, 32.4; LCMS ESI$^-$ (m/z): 310.2 $[M + H]^+$, LCMS purity 100.00% |

TABLE 1-continued

| | |
|---|---|
| C-3308 | Methyl 1-(4-acetamidophenyl)sulfonylaziridine-2-carboxylate<br>Molecular formula: $C_{12}H_{14}N_2O_5S$; Molecular weight: 298.31; Melting point: oil; $^1$H-NMR spectrum (400 MHz): ($CDCl_3$, HMDSO) δ: ($CDCl_3$, HMDSO) δ: 7.73-7.95 (m, 3H), 7.67 (d, J = 8.9 Hz, 2H), 3.74 (s, 3H), 3.43 (dd, J = 7.1, 4.1 Hz, 1H), 2.76 (d, J = 7.1 Hz, 1H), 2.56 (d, J = 4.1 Hz, 1H), 2.21 (s, 3H); $^{13}$C-NMR spectrum (100 MHz): ($CDCl_3$, HMDSO) δ: 168.9, 167.4, 143.4, 131.0, 129.5, 119.3, 53.0, 35.7, 32.1, 24.7; LCMS ESI$^+$ (m/z): 299.2 $[M + H]^+$, LCMS purity 94.91% |
| C-3311 | Methyl 1-(1-naphthylsulfonyl)aziridine-2-carboxylate<br>Molecular formula: $C_{14}H_{13}NO_4S$; Molecular weight: 291.32; Melting point: 102-104° C.; $^1$H-NMR spectrum (400 MHz): ($CDCl_3$, HMDSO) δ: 8.90 (ddd, J = 8.6, 1.8, 0.8 Hz, 1H), 8.24 (dd, J = 7.4, 1.3 Hz, 1H), 8.15 (dt, J = 8.2, 1.2 Hz, 1H), 7.95 (ddd, J = 8.2, 1.3, 0.6 Hz, 1H), 7.73 (ddd, J = 8.2, 6.9, 1.3 Hz, 1H), 7.63 (ddd, J = 8.2, 6.9, 1.2 Hz, 1H), 7.57 (dd, J = 8.2, 7.4 Hz, 1H), 3.70 (s, 3H), 3.49 (dd, J = 7.1, 4.1 Hz, 1H), 2.89 (d, J = 7.1 Hz, 1H), 2.59 (d, J = 4.1 Hz, 1H); $^{13}$C-NMR spectrum (100 MHz): ($CDCl_3$, HMDSO) δ: 167.1, 135.7, 134.2, 132.6, 130.0, 129.0, 128.7, 128.6, 127.2, 125.5, 124.0, 52.8, 35.9, 32.5; LCMS ESI+ (m/z): 292.3 [M + H]+, LCMS purity 98.48% |
| C-3314 | 1-(p-Tolylsulfonyl)aziridine-2-carbonitrile<br>Molecular formula: $C_{10}H_{10}N_2O_2S$; Molecular weight: 222.26; Melting point: 83-85° C.; $^1$H-NMR spectrum (400 MHz): ($CDCl_3$, HMDSO) δ: 7.85 (d, J = 8.4 Hz, 2H), 7.41 (d, J = 8.4 Hz, 2H), 3.22 (dd, J = 7.0, 4.0 Hz, 1H), 2.89 (d, J = 7.0 Hz, 1H), 2.65 (d, J = 4.0 Hz, 1H), 2.49 (s, 3H); $^{13}$C-NMR spectrum (100 MHz): ($CDCl_3$, HMDSO) δ: 146.1, 133.1, 130.2, 128.2, 115.0, 32.1, 23.4, 21.7; LCMS ESI- (m/z): 221.2 [M − H]−, LCMS purity 100.00% |
| C-3316 | Methyl 1-(4-cyclohexylphenyl)sulfonylaziridine-2-carboxylate<br>Molecular formula: $C_{16}H_{21}NO_4S$; Molecular weight: 323.12; Melting point: oil; $^1$H-NMR spectrum (400 MHz): ($CDCl_3$, HMDSO) δ: 7.87 (d, J = 8.5 Hz, 2H), 7.38 (d, J = 8.5 Hz, 2H), 3.74 (s, 3H), 3.36 (dd, J = 7.1, 4.1 Hz, 1H), 2.76 (d, J = 7.1 Hz, 1H), 2.56-2.65 (m, 1H), 2.56 (d, J = 4.1 Hz, 1H), 1.82-1.94 (m, 4H), 1.73-1.82 (m, 1H), 1.34-1.50 (m, 4H), 1.20-1.33 (m, 1H); $^{13}$C-NMR spectrum (100 MHz): ($CDCl_3$, HMDSO) δ: 167.3, 155.0, 134.1, 128.3, 127.7, 52.8, 44.6, 35.5, 34.0, 32.1, 26.6, 25.9; LCMS ESI$^+$ (m/z): 324.3 $[M + H]^+$, LCMS purity 98.89% |
| C-3319 | Methyl 1-(4-octylphenyl)sulfonylaziridine-2-carboxylate<br>Molecular formula: $C_{18}H_{27}NO_4S$; Molecular weight: 353.48; Melting point: oil; $^1$H-NMR spectrum (400 MHz): ($CDCl_3$, HMDSO) δ: 7.86 (d, J = 8.5 Hz, 2H), 7.36 (d, J = 8.5 Hz, 2H), 3.74 (s, 3H), 3.36 (dd, J = 7.1, 4.1 Hz, 1H), 2.77 (d, J = 7.1 Hz, 1H), 2.69 (t, J = 7.7 Hz, 2H), 2.56 (d, J = 4.1 Hz, 1H), 1.63 (quintet, J = 7.6 Hz, 2H), 1.22-1.36 (m, 10H), 0.88 (t, J = 7.1 Hz, 3H); $^{13}$C-NMR spectrum (100 MHz): ($CDCl_3$, HMDSO) δ: 167.3, 150.1, 134.1, 129.2, 128.2, 52.8, 35.9, 35.6, 32.1, 31.8, 31.0, 29.3, 29.1, 29.0, 22.6, 14.0; LCMS ESI$^+$ (m/z): 354.4 $[M + H]^+$, LCMS purity 100.00% |
| C-3320 | Methyl 1-(o-tolylsulfonyl)aziridine-2-carboxylate<br>Molecular formula: $C_{11}H_{13}NO_4S$; Molecular weight: 255.29; Melting point: oil; $^1$H-NMR spectrum (400 MHz): ($CDCl_3$, HMDSO) δ: 7.94 (dd, J = 7.8, 1.4 Hz, 1H), 7.53 (dt, J = 7.5, 1.4 Hz, 1H), 7.32-7.39 (m, 2H), 3.75 (s, 3H), 3.38 (dd, J = 7.1, 4.1 Hz, 1H), 2.83 (d, J = 7.1 Hz, 1H), 2.79 (s, 3H), 2.55 (d, J = 4.1 Hz, 1H); $^{13}$C-NMR spectrum (100 MHz): ($CDCl_3$, HMDSO) δ: 167.3, 139.4, 135.6, 134.0, 132.7, 129.5, 126.1, 52.8, 35.4, 32.2, 20.6; LCMS ESI$^+$ (m/z): 256.2 $[M + H]^+$, LCMS purity 100.00% |
| C-3324 | 1-[4-(Trifluoromethyl)phenyl]sulfonylaziridine-2-carboxamide<br>Molecular formula: $C_{10}H_9F_3N_2O_3S$; Molecular weight: 294.25; Melting point: 138-140° C.; $^1$H-NMR spectrum (400 MHz): (DMSO-$d_6$, HMDSO) δ: 8.19 (d, J = 8.3 Hz, 2H), 8.08 (d, J = 8.3 Hz, 2H), 7.86 (br s, 1H), 7.45 (br s, 1H), 3.36 (dd, J = 7.2, 4.5 Hz, 1H), 2.76 (d, J = 7.2, 1H), 2.56 (d, J = 4.5, 1H); $^{13}$C-NMR spectrum (100 MHz): (DMSO-$d_6$, HMDSO) δ: 166.6, 141.2, 133.9 (q, J = 32.7 Hz), 129.2, 127.3 (q, J = 3.6 Hz), 123.6 (q, J = 273.4 Hz), 37.5, 32.0; LCMS ESI$^+$ (m/z): 295.2 $[M + H]^+$, LCMS purity 100.00% |
| C-3326 | Methyl 1-[[5-(dimethylamino)-1-naphthyl]sulfonyl]aziridine-2-carboxylate<br>Molecular formula: $C_{16}H_{18}N_2O_4S$; Molecular weight: 334.39; Melting point: 117-119° C.; $^1$H-NMR spectrum (400 MHz): ($CDCl_3$, HMDSO) δ: 8.63 (dt, J = 8.5, 1.1 Hz, 1H), 8.55 (dt, J = 8.7, 0.9 Hz, 1H), 8.22 (dd, J = 7.4, 1.3 Hz, 1H), 7.61 (dd, J = 8.7, 7.6 Hz, 1H), 7.54 (dd, J = 8.5, 7.4 Hz, 1H), 7.21 (dd, J = 7.6, 0.9 Hz, 1H), 3.74 (s, 3H), 3.49 (dd, J = 7.1, 4.2 Hz, 1H), ), 2.89 (s, 6H), 2.87 (d, J = 7.1 Hz, 1H), 2.58 (d, J = 4.2 Hz, 1H); $^{13}$C-NMR spectrum (100 MHz): ($CDCl_3$, HMDSO) δ: 167.2, 151.7, 132.7, 131.9, 130.4, 129.9, 129.9, 128.7, 123.0, 120.0, 115.5, 52.8, 45.4, 35.8, 32.5; LCMS ESI$^+$ (m/z): 335.1 $[M + H]^+$, LCMS purity 100.00% |
| C-3327 | Methyl 1-[(6-methoxy-2-naphthyl)sulfonyl]aziridine-2-carboxylate<br>Molecular formula: $C_{15}H_{15}NO_5S$; Molecular weight: 321.35; Melting point: 97-99° C.; $^1$H-NMR spectrum (400 MHz): ($CDCl_3$, HMDSO) δ: 8.42-8.44 (m, 1H), 7.85-7.93 (m, 3H), 7.28 (dd, J = 9.0, 2.5 Hz, 1H), 7.20 (d, J = 2.5 Hz, 1H), 3.97 (s, 3H), 3.73 (s, 3H), 3.41 (dd, J = 7.1, 4.1 Hz, 1H), 2.82 (d, J = 7.1 Hz, 1H), 2.58 (d, J = 4.1 Hz, 1H); $^{13}$C-NMR spectrum (100 MHz): ($CDCl_3$, HMDSO) δ: 167.2, 160.4, 137.4, 131.3, 131.0, 129.8, 128.1, 127.3, 123.6, 120.9, 105.9, 55.5, 52.9, 35.7, 32.1; LCMS ESI$^+$ (m/z): 322.2 $[M + H]^+$, LCMS purity 95.29% |
| C-3329 | Methyl 1-[(6-methyl-2-naphthyl)sulfonyl]aziridine-2-carboxylate<br>Molecular formula: $C_{15}H_{15}NO_4S$; Molecular weight: 305.07; Melting point: 91-93° C.; $^1$H-NMR spectrum (400 MHz): ($CDCl_3$, HMDSO) δ: 8.63-8.66 (m, 1H), 8.21 (dd, J = 7.4, 1.3 Hz, 1H), 8.9 (dt, J = 8.2, 1.2 Hz, 1H), 7.84 (d, J = 1.4 Hz, 1H), 7.48 (dd, J = 8.2, 7.4 Hz, 1H), 7.46 (dd, J = 8.4, 1.6 Hz, 1H), 3.71 (s, 3H), 3.50 (dd, J = 7.1, 4.1 Hz, 1H), 2.88 (d, J = 7.1 Hz, 1H), 2.61 (s, 3H), 2.59 (d, J = 4.1 Hz, 1H); $^{13}$C-NMR spectrum (100 MHz): ($CDCl_3$, HMDSO) δ: 167.2, 138.9, 135.4, 132.5, 131.7, 130.0, 129.4, 129.2, 128.5, 124.4, 123.0, 52.8, 35.9, 32.5, 22.4; LCMS ESI$^+$ (m/z): 306.3 $[M + H]^+$, LCMS purity 98.42% |
| C-3332 | Methyl 1-(4-ethylphenyl)sulfonylaziridine-2-carboxylate<br>Molecular formula: $C_{12}H_{15}NO_4S$; Molecular weight: 269.07; Melting point: oil; $^1$H-NMR spectrum (400 MHz): ($CDCl_3$, HMDSO) δ: 7.87 (d, J = 8.4 Hz, 2H), 7.38 (d, J = 8.4 Hz, 2H), 3.74 (s, 3H), 3.35 (dd, J = 7.1, 4.1 Hz, 1H), 2.71-2.78 (m, 3H), 2.56 (d, J = 4.1 Hz, 1H), 1.27 (t, J = 7.6 Hz, 3H); $^{13}$C-NMR spectrum (100 MHz): ($CDCl_3$, HMDSO) δ: 167.2, 151.3, 134.1, 128.7, 128.3, 52.9, 35.6, 32.0, 28.9, 15.0; LCMS ESI$^+$ (m/z): 270.3 $[M + H]^+$, LCMS purity 97.57% |

TABLE 1-continued

| | |
|---|---|
| C-3336 | Methyl 1-[(4-methyl-1-naphthyl)sulfonyl]aziridine-2-carboxylate Molecular formula: $C_{15}H_{15}NO_4S$; Molecular weight: 305.07; Melting point: 96-98° C.; $^1$H-NMR spectrum (400 MHz): ($CDCl_3$, HMDSO) δ: 8.93 (d, J = 8.8 Hz, 1H), 8.13 (d, J = 7.6 Hz, 1H), 8.11 (dd, J = 8.0, 1.1 Hz, 1H), 7.72 (ddd, J = 8.3, 6.9 Hz, 1.4 Hz, 1H), 7.66 (ddd, J = 8.3, 6.9 Hz, 1.4 Hz, 1H), 7.41 (dd, J = 7.6, 0.9 Hz, 1H), 3.70 (s, 3H), 3.46 (dd, J = 7.1, 4.1 Hz, 1H), 2.86 (d, J = 7.1 Hz, 1H), 2.79 (s, 3H), 2.57 (d, J = 4.1 Hz, 1H); $^{13}$C-NMR spectrum (100 MHz): ($CDCl_3$, HMDSO) δ: 167.2, 143.2, 133.3, 130.7, 129.8, 129.0, 128.2, 127.0, 126.1, 124.8, 124.7, 52.8, 35.8, 32.4, 20.2; LCMS ESI$^+$ (m/z): 306.3 $[M + H]^+$, LCMS purity 100.00% |
| C-3342 | N,N-Dimethyl-1-(p-tolylsulfonyl)aziridine-2-carboxamide Molecular formula: $C_{12}H_{16}N_2O_3S$; Molecular weight: 268.33; Melting point: oil; $^1$H-NMR spectrum (400 MHz): ($CDCl_3$, HMDSO) δ: 7.85 (d, J = 8.4 Hz, 2H), 7.35 (d, J = 8.4 Hz, 2H), 3.59 (dd, J = 6.9, 4.2 Hz, 1H), 3.22 (s, 3H), 2.97 (s, 3H), 2.68 (d, J = 4.2 Hz, 1H), 2.64 (d, J = 6.9 Hz, 1H), 2.45 (s, 3H); $^{13}$C-NMR spectrum (100 MHz): ($CDCl_3$, HMDSO) δ: 164.9, 145.1, 134.2, 129.8, 128.1, 37.2, 36.0, 35.2, 32.4, 21.6; LCMS ESI$^+$ (m/z): 269.2 $[M + H]^+$, LCMS purity 100.00% |
| C-3343 | Methyl 1-[4-(dimethylamino)phenyl]sulfonylaziridine-2-carboxylate Molecular formula: $C_{12}H_{16}N_2O_4S$; Molecular weight: 284.33; Melting point: 84-86° C.; $^1$H-NMR spectrum (400 MHz): ($CDCl_3$, HMDSO) δ: 7.74 (d, J = 9.1 Hz, 2H), 6.68 (d, J = 9.1 Hz, 2H), 3.73 (s, 3H), 3.25 (dd, J = 7.1, 4.1 Hz, 1H), 3.07 (s, 6H), 2.67 (d, J = 7.1 Hz, 1H), 2.50 (d, J = 4.1 Hz, 1H); $^{13}$C-NMR spectrum (100 MHz): ($CDCl_3$, HMDSO) δ: 167.6, 153.7, 130.1, 121.1, 110.9, 52.7, 40.0, 35.5, 31.8; LCMS ESI$^+$ (m/z): 285.2 $[M + H]^+$, LCMS purity 100.00% |
| C-3346 | Methyl 1-(2-furylsulfonyl)aziridine-2-carboxylate Molecular formula: $C_8H_9NO_5S$; Molecular weight: 231.02; Melting point: oil; $^1$H-NMR spectrum (400 MHz): ($CDCl_3$, HMDSO) δ: 7.67 (dd, J = 1.8, 1.0 Hz, 1H), 7.23 (dd, J = 3.5, 1.0 Hz, 1H), 6.58 (dd, J = 3.5, 1.8 Hz, 1H), 3.78 (s, 3H), 3.42 (dd, J = 7.1, 4.2 Hz, 1H), 2.85 (d, J = 7.1 Hz, 1H), 2.68 (d, J = 4.2 Hz, 1H); $^{13}$C-NMR spectrum (100 MHz): ($CDCl_3$, HMDSO) δ: 166.8, 147.9, 145.5, 111.6, 53.0, 35.9, 32.3; LCMS ESI$^+$ (m/z): 232.1 $[M + H]^+$, LCMS purity 99.01% |
| C-3350 | Methyl 1-[(2-oxo-1H-quinolin-6-yl)sulfonyl]aziridine-2-carboxylate Molecular formula: $C_{13}H_{12}N_5O_5S$; Molecular weight: 308.31; Melting point: 139-141° C.; $^1$H-NMR spectrum (400 MHz): ($CDCl_3$, HMDSO) δ: 12.78 (br s, 1H), 8.24 (d, J = 2.0 Hz, 1H), 8.05 (dd, J = 8.7, 2.0 Hz, 1H), 7.90 (d, J = 9.6 Hz, 1H), 7.67 (d, J = 8.7 Hz, 1H), 6.84 (d, J = 9.6 Hz, 1H), 3.74 (s, 3H), 3.41 (dd, J = 7.1, 4.1 Hz, 1H), 2.84 (d, J = 7.1 Hz, 1H), 2.61 (d, J = 4.1 Hz, 1H); $^{13}$C-NMR spectrum (100 MHz): ($CDCl_3$, HMDSO) δ: 167.0, 164.6, 142.0, 140.7, 131.1, 129.4, 129.1, 123.4, 119.4, 117.1, 53.0, 35.9, 32.2; LCMS ESI$^+$ (m/z): 309.1 $[M + H]^+$, LCMS purity 96.88% |
| C-3353 | Methyl 1-(2,4-difluorophenyl)sulfonylaziridine-2-carboxylate Molecular formula: $C_{10}H_9F_2NO_4S$; Molecular weight: 277.24; Melting point: 40-42° C.; $^1$H-NMR spectrum (400 MHz): ($CDCl_3$, HMDSO) δ: 7.99 (ddd, J = 7.9, 7.9, 7.9 Hz, 1H), 7.03-7.08 (m, 1H), 6.97-7.03 (m, 1H), 3.77 (s, 3H), 3.52 (ddd, J = 7.2, 4.3, 0.9 Hz, 1H), 2.97 (dd, J = 7.2, 1.2 Hz, 1H), 2.69 (d, J = 4.3 Hz, 1H); $^{13}$C-NMR spectrum (100 MHz): ($CDCl_3$, HMDSO) δ: 166.9, 166.7 (dd, J = 260.0, 11.6 Hz,), 160.5 (dd, J = 261.0, 12.9 Hz,), 132.4 (d, J = 10.8 Hz,), 122.1 (dd, J = 14.5, 3.4 Hz,), 112.2 (dd, J = 22.3, 3.5 Hz,), 106.0 (t, J = 25.5 Hz,), 53.0, 36.1, 32.6; LCMS ESI$^+$ (m/z): 276.3 $[M + H]^+$, LCMS purity 98.27% |
| C-3355 | Methyl 1-(2-oxochromen-6-yl)sulfonylaziridine-2-carboxylate Molecular formula: $C_{13}H_{11}NO_6S$; Molecular weight: 309.29; Melting point: 42-44° C.; $^1$H-NMR spectrum (400 MHz): ($CDCl_3$, HMDSO) δ: 12.78 (br s, 1H), 8.24 (d, J = 2.0 Hz, 1H), 8.05 (dd, J = 8.7, 2.0 Hz, 1H), 7.90 (d, J = 9.6 Hz, 1H), 7.67 (d, J = 8.7 Hz, 1H), 6.84 (d, J = 9.6 Hz, 1H), 3.74 (s, 3H), 3.41 (dd, J = 7.1, 4.1 Hz, 1H), 2.84 (d, J = 7.1 Hz, 1H), 2.61 (d, J = 4.1 Hz, 1H); $^{13}$C-NMR spectrum (100 MHz): ($CDCl_3$, HMDSO) δ: 166.8, 159.0, 157.3, 142.1, 133.4, 131.0, 128.7, 119.1, 118.7, 118.2, 53.0, 36.0, 32.3; LCMS ESI$^+$ (m/z): 310.1 $[M + H]^+$, LCMS purity 100.00% |
| C-3357 | 1-[4-(Dimethylamino)phenyl]sulfonyl-N,N-dimethyl-aziridine-2-carboxamide Molecular formula: $C_{13}H_{19}N_3O_3S$; Molecular weight: 297.37; Melting point: 144-146° C.; $^1$H-NMR spectrum (400 MHz): ($CDCl_3$, HMDSO) δ: 7.74 (d, J = 9.2 Hz, 2H), 6.68 (d, J = 9.2 Hz, 2H), 3.49 (dd, J = 6.9, 4.2 Hz, 1H), 3.23 (s, 3H), 3.06 (s, 6H), 2.97 (s, 3H), 2.61 (d, J = 4.2 Hz, 1H), 2.55 (d, J = 6.9 Hz, 1H); $^{13}$C-NMR spectrum (100 MHz): ($CDCl_3$, HMDSO) δ: 165.3, 153.6, 130.0, 121.4, 110.8, 40.0, 37.3, 36.0, 35.4, 31.9; LCMS ESI$^+$ (m/z): 298.2 $[M + H]^+$, LCMS purity 100.00% |
| C-3362 | 1-(4-Butylphenyl)sulfonyl-N,N-dimethyl-aziridine-2-carboxamide Molecular formula: $C_{15}H_{22}N_2O_3S$; Molecular weight: 310.41; Melting point: oil; $^1$H-NMR spectrum (400 MHz): ($CDCl_3$, HMDSO) δ: 7.86 (d, J = 8.4 Hz, 2H), 7.35 (d, J = 8.4 Hz, 2H), 3.59 (dd, J = 6.9, 4.2 Hz, 1H), 3.22 (s, 3H), 2.98 (s, 3H), 2.69 (t, J = 7.6 Hz, 2H), 2.68 (d, J = 4.2 Hz, 1H), 2.65 (d, J = 6.9 Hz, 1H), 1.57-1.66 (m, 2H), 1.35 (sextet, J = 7.5 Hz, 2H), 0.93 (d, J = 7.4 Hz, 3H); $^{13}$C-NMR spectrum (100 MHz): ($CDCl_3$, HMDSO) δ: 164.9, 150.0, 134.3, 129.2, 128.2, 37.2, 36.0, 35.6, 35.2, 33.1, 32.5, 22.2, 13.8; LCMS ESI$^+$ (m/z): 311.2 $[M + H]^+$, LCMS purity 100.00% |
| C-3364 | 1-(4-Isopropylphenyl)sulfonyl-N,N-dimethyl-aziridine-2-carboxamide Molecular formula: $C_{14}H_{20}N_2O_3S$; Molecular weight: 296.38; Melting point: oil; $^1$H-NMR spectrum (400 MHz): ($CDCl_3$, HMDSO) δ: 7.88 (d, J = 8.5 Hz, 2H), 7.40 (d, J = 8.5 Hz, 2H), 3.55 (dd, J = 6.9, 4.2 Hz, 1H), 3.23 (s, 3H), 3.00 (septet, J = 6.9 Hz, 1H), 2.98 (s, 3H), 2.69 (d, J = 4.2 Hz, 1H), 2.65 (d, J = 6.9 Hz, 1H), 1.28 (d, J = 6.9 Hz, 6H); $^{13}$C-NMR spectrum (100 MHz): ($CDCl_3$, HMDSO) δ: 164.9, 155.8, 134.5, 128.3, 127.3, 37.2, 36.0, 35.2, 34.3, 32.6, 23.6; LCMS ESI$^+$ (m/z): 297.2 $[M + H]^+$, LCMS purity 100.00% |

TABLE 1-continued

| | |
|---|---|
| C-3365 | N,N-Dimethyl-1-(1-naphthylsulfonyl)aziridine-2-carboxamide<br>Molecular formula: $C_{15}H_{16}N_2O_3S$; Molecular weight: 304.36; Melting point: 110-112° C.; $^1$H-NMR spectrum (400 MHz): ($CDCl_3$, HMDSO) δ: 8.87 (ddd, J = 8.5, 1.8, 0.9 Hz, 1H), 8.25 (dd, J = 7.4, 1.3 Hz, 1H), 8.15 (dt, J = 8.2, 1.2 Hz, 1H), 7.95 (ddd, J = 8.2, 1.3, 0.6 Hz, 1H), 7.72 (ddd, J = 8.5, 6.9, 1.4 Hz, 1H), 7.63 (ddd, J = 8.2, 6.9, 1.2 Hz, 1H), 7.56 (dd, J = 8.2, 7.4 Hz, 1H), 3.75 (dd, J = 6.9, 4.3 Hz, 1H), 3.20 (s, 3H), 2.97 (s, 3H), 2.74 (d, J = 6.9 Hz, 1H), 2.69 (d, J = 4.3 Hz, 1H); $^{13}$C-NMR spectrum (100 MHz): ($CDCl_3$, HMDSO) δ: 164.9, 135.6, 134.2, 132.8, 129.7, 129.0, 128.7, 128.7, 127.2, 125.7, 123.9, 37.2, 36.0, 35.8, 32.7; LCMS ESI$^+$ (m/z): 305.2 $[M + H]^+$, LCMS purity 96.57% |
| C-3366 | N,N-Dimethyl-1-[(4-methyl-1-naphthyl)sulfonyl]aziridine-2-carboxamide<br>Molecular formula: $C_{16}H_{18}N_2O_3S$; Molecular weight: 318.39; Melting point: 120-122° C.; $^1$H-NMR spectrum (400 MHz): ($CDCl_3$, HMDSO) δ: 8.92 (ddd, J = 8.3, 1.4, 0.7 Hz, 1H), 8.14 (d, J = 7.6 Hz, 1H), 8.10 (ddd, J = 8.3, 1.3, 0.7 Hz, 1H), 7.71 (ddd, J = 8.3, 6.8, 1.5 Hz, 1H), 7.66 (ddd, J = 8.3, 6.9, 1.5 Hz, 1H), 7.41 (ddd, J = 7.6, 1.9, 0.9 Hz, 1H), 3.73 (dd, J = 6.9, 4.3 Hz, 1H), 3.20 (s, 3H), 2.97 (s, 3H), 2.79 (s, 3H), 2.70 (d, J = 6.9 Hz, 1H), 2.66 (d, J = 4.3 Hz, 1H); $^{13}$C-NMR spectrum (100 MHz): ($CDCl_3$, HMDSO) δ: 164.9, 143.1, 133.3, 130.9, 129.7, 129.0, 128.2, 127.0, 126.2, 124.8, 124.7, 37.3, 35.9, 35.9, 32.6, 20.2; LCMS ESI$^+$ (m/z): 319.2 $[M + H]^+$, LCMS purity 98.41% |
| C-3368 | N,N-Dimethyl-1-(4-pentylphenyl)sulfonyl-aziridine-2-carboxamide<br>Molecular formula: $C_{16}H_{24}N_2O_3S$; Molecular weight: 324.44; Melting point: oil; $^1$H-NMR spectrum (400 MHz): ($CDCl_3$, HMDSO) δ: 7.85 (d, J = 8.5 Hz, 2H), 7.30 (d, J = 8.5 Hz, 2H), 3.59 (dd, J = 6.9, 4.3 Hz, 1H), 3.21 (s, 3H), 2.97 (s, 3H), 2.68 (t, J = 7.8 Hz, 2H), 2.68 (d, J = 4.3 Hz, 1H), 2.65 (d, J = 6.9 Hz, 1H), 1.63 (quintet, J = 7.5 Hz, 2H), 1.23-1.39 (m, 4H), 0.89 (t, J = 7.0 Hz, 3H); $^{13}$C-NMR spectrum (100 MHz): ($CDCl_3$, HMDSO) δ: 164.9, 150.0, 134.4, 129.2, 128.2, 37.2, 36.0, 35.9, 35.2, 32.5, 31.3, 30.7, 22.4, 13.9; LCMS ESI$^+$ (m/z): 325.2 $[M + H]^+$, LCMS purity 100.00% |
| C-3369 | 1-(4-Hexylphenyl)sulfonyl-N,N-dimethyl-aziridine-2-carboxamide<br>Molecular formula: $C_{17}H_{26}N_2O_3S$; Molecular weight: 338.46; Melting point: oil; $^1$H-NMR spectrum (400 MHz): ($CDCl_3$, HMDSO) δ: 7.86 (d, J = 8.5 Hz, 2H), 7.34 (d, J = 8.5 Hz, 2H), 3.59 (dd, J = 6.9, 4.2 Hz, 1H), 3.21 (s, 3H), 2.97 (s, 3H), 2.68 (t, J = 7.8 Hz, 2H), 2.68 (d, J = 4.2 Hz, 1H), 2.65 (d, J = 6.9 Hz, 1H), 1.62 (quintet, J = 7.5 Hz, 2H), 1.23-1.37 (m, 6H), 0.88 (t, J = 7.0 Hz, 3H); $^{13}$C-NMR spectrum (100 MHz): ($CDCl_3$, HMDSO) δ: 165.0, 150.0, 134.3, 129.2, 128.2, 37.2, 36.0, 35.9, 35.2, 32.5, 31.6, 30.9, 28.8, 22.5, 14.0; LCMS ESI$^+$ (m/z): 339.2 $[M + H]^+$, LCMS purity 95.86% |
| C-3371 | 1-[[5-(Dimethylamino)-1-naphthyl]sulfonyl]-N,N-dimethylaziridine-2-carboxamide<br>Molecular formula: $C_{17}H_{21}N_3O_3S$; Molecular weight: 347.43; Melting point: oil; $^1$H-NMR spectrum (400 MHz): ($CDCl_3$, HMDSO) δ: 8.62 (dt, J = 8.5, 1.1 Hz, 1H), 8.55 (dt, J = 8.7, 0.9 Hz, 1H), 8.23 (dd, J = 7.4, 1.3 Hz, 1H), 7.60 (dd, J = 8.7, 7.6 Hz, 1H), 7.53 (dd, J = 8.5, 7.4 Hz, 1H), 7.21 (dd, J = 7.6, 0.9 Hz, 1H), 3.74 (dd, J = 6.9, 4.3 Hz, 1H), 3.20 (s, 3H), 2.96 (s, 3H), 2.88 (s, 6H), 2.73 (d, J = 6.9 Hz, 1H), 2.68 (d, J = 4.3 Hz, 1H); $^{13}$C-NMR spectrum (100 MHz): ($CDCl_3$, HMDSO) δ: 164.9, 151.6, 132.9, 131.8, 130.4, 129.9, 129.7, 128.7, 122.9, 120.1, 115.5, 45.4, 37.3, 35.9, 35.8, 32.7; LCMS ESI$^+$ (m/z): 348.2 $[M + H]^+$, LCMS purity 95.88% |
| C-3373 | N,N-Dimethyl-1-(2-naphthylsulfonyl)aziridine-2-carboxamide<br>Molecular formula: $C_{15}H_{16}N_2O_3S$; Molecular weight: 304.36; Melting point: oil<br>$^1$H-NMR spectrum (400 MHz): ($CDCl_3$) δ: 8.54-8.52 (m, 1H), 8.04-7.90 (m, 4H), 7.73-7.59 (m, 2H), 3.67 (dd, J = 6.9, 4.3 Hz, 1H), 3.24 (s, 3H), 2.98 (s, 3H), 2.74 (d, J = 6.9 Hz, 1H), 2.72 (d, J = 4.3 Hz, 1H); $^{13}$C-NMR spectrum (100 MHz): ($CDCl_3$, HMDSO) δ: 165.0, 135.6, 134.3, 132.1, 129.9, 129.7, 129.6, 128.2, 127.9, 123.1, 37.4, 36.2, 35.5, 32.8<br>LCMS ESI+ (m/z): 305.2 [M + H]+. LCMS purity 97.08% |
| C-3374 | N,N-Dimethyl-1-[4-(trifluoromethyl)phenyl]sulfonyl-aziridine-2-carboxamide<br>Molecular formula: $C_{12}H_{13}N_2O_3S$; Molecular weight: 322.30; Melting point: oil; $^1$H-NMR spectrum (400 MHz): 8.12 (d, J = 8.4 Hz, 2H), 7.83 (d, J = 8.4 Hz, 2H), 3.68 (dd, J = 6.9, 4.3 Hz, 1H), 3.25 (s, 3H), 3.00 (s, 3H), 2.75 (d, J = 4.3 Hz, 1H), 2.73 (d, J = 6.9 Hz, 1H); $^{13}$C-NMR spectrum (100 MHz): ($CDCl_3$, HMDSO) δ: 164.4, 141.1, 135.6 (q, J = 33.3 Hz), 128.6, 126.3 (q, J = 3.7 Hz), 123.0 (q, J = 273.2 Hz), 37.2, 36.0, 35.3, 33.0; LCMS ESI$^+$ (m/z): 323.1 $[M + H]^+$, LCMS purity 95.04.00% |
| C-3375 | Methyl 1-[[6-(dimethylamino)-1-naphthyl]sulfonyl]aziridine-2-carboxylate<br>Molecular formula: $C_{16}H_{18}N_2O_4S$; Molecular weight: 334.39; Melting point: 106-108° C.<br>$^1$H-NMR spectrum (400 MHz): ($CDCl_3$, HMDSO) δ: 8.73 (dt, J = 9.5, 0.6 Hz, 1H), 7.93 (d, J = 8.3 Hz, 1H), 7.89 (dd, J = 7.3, 1.2 Hz, 1H), 7.40 (dd, J = 8.3, 7.3 Hz, 1H), 7.34 (dd, J = 9.5, 2.6 Hz, 1H), 6.94 (d, J = 2.6 Hz, 1H), 3.70 (s, 3H), 3.44 (dd, J = 7.1, 4.1 Hz, 1H), ), 3.09 (s, 6H), 2.83 (d, J = 7.1 Hz, 1H), 2.55 (d, J = 4.2 Hz, 1H); $^{13}$C-NMR spectrum (100 MHz): ($CDCl_3$, HMDSO) δ: 167.3, 148.9, 136.2, 133.8, 132.1, 126.2, 125.6, 124.1, 121.6, 118.2, 106.2, 52.7, 40.4, 35.7, 32.3<br>LCMS ESI$^+$ (m/z): 335.1 $[M + H]^+$, LCMS purity 100% |
| C-3376 | Methyl 1-[[6-(dimethylamino)-5-formyl-1-naphthyl]sulfonyl]aziridine-2-carboxylate<br>Molecular formula: $C_{17}H_{18}N_2O_5S$; Molecular weight: 362.40; Melting point: 116-117° C.; $^1$H-NMR spectrum (400 MHz): ($CDCl_3$, HMDSO) δ: 10.30 (s, 1H), 9.49 (dt, J = 8.7, 1.1 Hz, 1H), 9.02 (dd, J = 9.7, 0.9 Hz, 1H), 8.05 (dd, J = 7.4, 1.1 Hz, 1H), 7.62 (dd, J = 8.7, 7.4 Hz, 1H), 7.53 (d, J = 9.7 Hz, 1H), 3.72 (s, 3H), 3.47 (dd, J = 7.1, 4.1 Hz, 1H), 3.19 (s, 6H), 2.85 (d, J = 7.1 Hz, 1H), 2.55 (d, J = 4.2 Hz, 1H); $^{13}$C-NMR spectrum (100 MHz): ($CDCl_3$, HMDSO) δ: 190.8, 167.1, 158.1, 133.9, 132.6, 132.0, 131.3, 127.2, 127.0, 123.7, 120.4, 116.4, 52.8, 45.9, 35.8, 32.4; LCMS ESI$^+$ (m/z): 363.1 $[M + H]^+$, LCMS purity 100.00% |

TABLE 1-continued

| | |
|---|---|
| C-3377 | 1-[[6-(Dimethylamino)-1-naphthyl]sulfonyl]-N,N-dimethylaziridine-2-carboxamide<br>Molecular formula: $C_{17}H_{21}N_3O_3S$; Molecular weight: 347.43; Melting point: 147-149° C.<br>1H-NMR spectrum (400 MHz): ($CDCl_3$, HMDSO) δ: 8.72 (d, J = 9.5 Hz, 1H), 7.90 (d, J = 8.4 Hz, 1H), 7.89 (dd, J = 7.3, 1.2 Hz, 1H), 7.49 (dd, J = 8.2, 7.5 Hz, 1H), 7.32 (dd, J = 9.5, 2.7 Hz, 1H), 6.93 (d, J = 2.7 Hz, 1H), 3.67 (dd, J = 6.9, 4.3 Hz, 1H), 3.14 (s, 3H), 3.08 (s, 6H), 2.94 (s, 3H), 2.71 (d, J = 6.9 Hz, 1H), 2.67 (d, J = 4.3 Hz, 1H); $^{13}C$-NMR spectrum (100 MHz): ($CDCl_3$, HMDSO) δ: 165.0, 148.9, 136.2, 133.7, 132.3, 126.3, 125.3, 124.1, 121.5, 118.2, 106.1, 40.3, 37.1, 35.9, 35.9, 32.3<br>LCMS ESI+ (m/z): 348.1 [M + H]+, LCMS purity 100% |
| C-3380 | 1-(4-Hexylphenyl)sulfonyl-N-methyl-aziridine-2-carboxamide<br>Molecular formula: $C_{16}H_{24}N_2O_3S$; Molecular weight: 324.44; Melting point: 84-86° C.; $^1H$-NMR spectrum (400 MHz): ($CDCl_3$, HMDSO) δ: 7.83 (d, J = 8.5 Hz, 2H), 7.38 (d, J = 8.5 Hz, 2H), 6.15 (br s, 1H), 3.28 (dd, J = 7.7, 4.2 Hz, 1H), 2.75 (d, J = 4.9 Hz, 3H), 2.74 (d, J = 7.7 Hz, 1H), 2.71 (t, J = 7.8 Hz, 2H), 2.36 (d, J = 4.2 Hz, 1H), 1.64 (quintet, J = 7.5 Hz, 2H), 1.25-1.39 (m, 6H), 0.89 (t, J = 7.0 Hz, 3H); $^{13}C$-NMR spectrum (100 MHz): ($CDCl_3$, HMDSO) δ: 166.2, 150.4, 133.4, 129.4, 128.2, 37.9, 36.0, 33.4, 31.5, 30.8, 28.8, 25.9, 22.5, 14.0; LCMS $ESI^+$ (m/z): 325.1 $[M + H]^+$, LCMS purity 97.38% |
| C-3383 | Methyl 1-[[4-(dimethylamino)-1-naphthyl]sulfonyl]aziridine-2-carboxylate<br>Molecular formula: $C_{16}H_{18}N_2O_4S$; Molecular weight: 334.39; Melting point: oil; $^1H$-NMR spectrum (400 MHz): ($CDCl_3$, HMDSO) δ: 8.86 (ddd, J = 8.6, 1.3, 0.7 Hz, 1H), 8.23 (ddd, J = 8.6, 1.4, 0.7 Hz, 1H), 8.11 (d, J = 8.3 Hz, 1H), 7.67 (ddd, J = 8.6, 6.9, 1.4 Hz, 1H), 7.56 (ddd, J = 8.6, 6.9, 1.3 Hz, 1H), 6.97 (d, J = 8.3 Hz, 1H), 3.70 (s, 3H), 3.44 (dd, J = 7.1, 4.1 Hz, 1H), 3.01 (s, 6H), 2.83 (d, J = 7.1 Hz, 1H), 2.54 (d, J = 4.1 Hz, 1H); $^{13}C$-NMR spectrum (100 MHz): ($CDCl_3$, HMDSO) δ: 167.4, 157.5, 131.3, 130.8, 128.3, 128.2, 125.9, 125.7, 125.3, 124.3, 110.7, 52.7, 44.6, 35.7, 32.4; LCMS $ESI^+$ (m/z): 335.1 $[M + H]^+$, LCMS purity 100.00% |
| C-3384 | 1-(4-Cyclohexylphenyl)sulfonyl-N,N-dimethyl-aziridine-2-carboxamide<br>Molecular formula: $C_{17}H_{24}N_2O_3S$; Molecular weight: 336.45; Melting point: oil; $^1H$-NMR spectrum (400 MHz): ($CDCl_3$, HMDSO) δ: 7.86 (d, J = 8.5 Hz, 2H), 7.37 (d, J = 8.5 Hz, 2H), 3.58 (dd, J = 6.9, 4.3 Hz, 1H), 3.21 (s, 3H), 2.97 (s, 3H), 2.68 (d, J = 4.3 Hz, 1H), 2.65 (d, J = 6.9 Hz, 1H), 2.54-2.63 (m, 1H), 1.80-1.92 (m, 4H), 1.72-1.80 (m, 1H), 1.32-1.48 (m, 4H), 1.19-1.32 (m, 1H); $^{13}C$-NMR spectrum (100 MHz): ($CDCl_3$, HMDSO) δ: 164.9, 154.9, 134.4, 128.2, 127.7, 44.6, 37.3, 36.0, 35.1, 34.0, 32.5, 26.6, 25.9; LCMS $ESI^+$ (m/z): 337.2 $[M + H]^+$, LCMS purity 95.84% |
| C-3385 | 1-[[4-(Dimethylamino)-1-naphthyl]sulfonyl]-N,N-dimethylaziridine-2-carboxamide<br>Molecular formula: $C_{17}H_{21}N_3O_3S$; Molecular weight: 347.43; Melting point: 120-122° C.<br>$^1H$-NMR spectrum (400 MHz): ($CDCl_3$, HMDSO) δ: 8.85 (ddd, J = 8.6, 1.3, 0.6 Hz, 1H), 8.22 (ddd, J = 8.6, 1.3, 0.6 Hz, 1H), 8.12 (d, J = 8.2 Hz, 1H), 7.65 (ddd, J = 8.6, 6.9, 1.4 Hz, 1H), 7.56 (ddd, J = 8.6, 6.9, 1.4 Hz, 1H), 6.97 (d, J = 8.2 Hz, 1H), 3.69 (dd, J = 6.9, 4.3 Hz, 1H), 3.20 (s, 3H), 3.01 (s, 6H), 2.96 (s, 3H), 2.68 (d, J = 6.9 Hz, 1H), 2.64 (d, J = 4.3 Hz, 1H); $^{13}C$-NMR spectrum (100 MHz): ($CDCl_3$, HMDSO) δ: 165.2, 157.4, 131.0, 130.8, 128.3, 128.2, 126.0, 125.7, 125.3, 124.6, 110.6, 44.6, 37.3, 35.9, 35.8, 32.5<br>LCMS $ESI^+$ (m/z): 348.1 $[M + H]^+$, LCMS purity 100% |
| C-3389 | 1-(4-Hexylphenyl)sulfonylaziridine-2-carboxamide<br>Molecular formula: $C_{15}H_{22}N_2O_3S$; Molecular weight: 310.41; Melting point: 103-105° C.; $^1H$-NMR spectrum (400 MHz): (DMSO-$d_6$, HMDSO) δ: 7.84 (d, J = 8.4 Hz, 2H), 7.81 (br s, 1H), 7.50 (d, J = 8.4 Hz, 2H), 7.41 (br s, 1H), 3.23 (dd, J = 7.2, 4.3 Hz, 1H), 2.69 (t, J = 7.7 Hz, 2H), 2.62 (d, J =7.2 Hz, 1H), 2.46 (d, J = 4.3 Hz, 1H), 1.60 (quintet, J = 7.4 Hz, 2H), 1.22-1.33 (m, 6H), 0.85 (t, J = 7.0 Hz, 3H); $^{13}C$-NMR spectrum (100 MHz): (DMSO-$d_6$, HMDSO) δ: 167.0, 150.0, 134.5, 129.8, 128.2, 37.1, 35.4, 31.6, 31.4, 30.9, 28.7, 22.4, 14.3; LCMS $ESI^+$ (m/z): 311.1 $[M + H]^+$, LCMS purity 100.00% |
| C-3390 | Methyl 1-[[6-(dimethylamino)-5-formyl-2-naphthyl]sulfonyl]aziridine-2-calboxylate<br>Molecular formula: $C_{17}H_{18}N_2O_5S$; Molecular weight: 362.40; Melting point: 147-149° C.<br>$^1H$-NMR spectrum (400 MHz): (CDCl3, HMDSO) δ: 10.27 (s, 1H), 9.22 (d, J = 9.1 Hz, 1H), 8.35 (d, J = 2.0 Hz, 1H), 7.96 (dd, J = 9.1, 2.0 Hz, 1H), 7.94 (d, J = 9.1 Hz, 1H), 7.41 (d, J = 9.1 Hz, 1H), 3.72 (s, 3H), 3.39 (dd, J = 7.1, 4.1 Hz, 1H), 3.24 (s, 6H), 2.81 (d, J = 7.1 Hz, 1H), 2.58 (d, J = 4.1 Hz, 1H); $^{13}C$-NMR spectrum (100 MHz): (CDCl3, HMDSO) δ: 190.1, 167.2, 159.5, 135.9, 135.7, 131.1, 129.7, 126.5, 126.1, 125.1, 119.6, 115.2, 52.9, 45.7, 35.8, 32.0<br>LCMS $ESI^+$ (m/z): 363.1 $[M + H]^+$, LCMS purity 96.10% |
| C-3391 | 1-[[6-(Dimethylamino)-5-formyl-2-naphthyl]sulfonyl]-N,N-dimethylaziridine-2-carboxamide<br>Molecular formula: $C_{18}H_{21}N_3O_4S$; Molecular weight: 375.44; Melting point: 58-60° C.; $^1H$-NMR spectrum (400 MHz): ($CDCl_3$, HMDSO) δ: 10.27 (s, 1H), 9.21 (dt, J = 9.2, 0.6 Hz, 1H), 8.35 (d, J = 2.1 Hz, 1H), 7.97 (dd, J = 9.2, 2.1 Hz, 1H), 7.94 (d, J = 9.2 Hz, 1H), 7.41 (d, J = 9.2 Hz, 1H), 3.64 (dd, J = 6.9, 4.3 Hz, 1H), 3.24 (s, 3H), 3.23 (s, 6H), 2.97 (s, 3H), 2.70 (d, J = 6.9 Hz, 1H), 2.69 (d, J = 4.3 Hz, 1H); $^{13}C$-NMR spectrum (100 MHz): ($CDCl_3$, HMDSO) δ: 190.1, 164.9, 159.5, 135.8, 135.6, 131.5, 129.5, 126.5, 126.1, 125.0, 119.6, 115,2, 45.7, 37.2, 36.0, 35.3, 32.5; LCMS $ESI^+$ (m/z): 376.1 $[M + H]^+$, LCMS purity 100.00% |
| C-3393 | Methyl 1-[[5-chloro-6-(methylamino)-2-naphthyl]sulfonyl]aziridine-2-carboxylate<br>Molecular formula: $C_{15}H_{15}ClN_2O_4S$; Molecular weight: 354.81; Melting point: 170-172° C.; $^1H$-NMR spectrum (400 MHz): ($CDCl_3$, HMDSO) δ: 8.36 (d, J = 1.9 Hz, 1H), 8.12 (dt, J = 9.1, 0.6 Hz, 1H), 7.90 (dd, J = 9.1, 2.0 Hz, 1H), 7.83 (d, J = 9.0 Hz, 1H), 7.19 (d, J = 9.0 Hz, 1H), 5.01 (q, J = 5.1 Hz, 1H), 3.72 (s, 3H), 3.39 (dd, J = 7.1, 4.1 Hz, 1H), 3.09 (d, J = 5.1 Hz, 3H), 2.81 (d, J = 7.1 Hz, 1H), 2.56 (d, J = 4.1 Hz, 1H); $^{13}C$-NMR spectrum (100 MHz): ($CDCl_3$, HMDSO) δ: 167.3, 145.4, 133.9, 130.5, 129.7, 129.1, 125.3, 124.4, 123.3, 114.3, 110.5, 52.8, 35.7, 32.0, 30.3;<br>LCMS $ESI^+$ (m/z): 355.0 $[M + H]^+$, LCMS purity 100.00% |
| C-3397 | Methyl 1-[[6-(dimethylamino)-2-naphthyl]sulfonyl]aziridine-2-carboxylate<br>Molecular formula: $C_{16}H_{18}N_2O_4S$; Molecular weight: 334.39; Melting point: 156-158° C.; $^1H$-NMR spectrum (400 MHz): ($CDCl_3$, HMDSO) δ: 8.31 (d, J = 1.9 Hz, 1H), 7.92 (d, J = 9.2 Hz, 1H), 7.77 (dd, J = 8.8, 1.9 Hz, 1H), 7.71 (d, J = 8.8 Hz, 1H), 7.22 (dd, J = 9.2, 2.6 Hz, 1H), 6.88 (d, J = 2.6 Hz, 1H), 3.72 (s, 3H), 3.36 (dd, J = 7.1, 4.1 Hz, 1H), 3.13 (s, 6H), 2.78 (d, J = 7.1 Hz, 1H), 2.56 (d, J = 4.1 Hz, 1H); $^{13}C$-NMR spectrum (100 MHz): ($CDCl_3$, HMDSO) δ: 167.4, 150.7, |

TABLE 1-continued

| | |
|---|---|
| | 137.7, 130.5, 130.0, 128.1, 127.0, 124.4, 123.4, 116.3, 104.9, 52.8, 40.3, 35.6, 32.0; LCMS ESI$^+$ (m/z): 335.1 $[M + H]^+$, LCMS purity 100.00% |
| C-3398 | 1-[[6-(Dimethylamino)-2-naphthyl]sulfonyl]-N,N-dimethylaziridine-2-carboxamide<br>Molecular formula: $C_{17}H_{21}N_3O_3S$; Molecular weight: 347.43; Melting point: foam; $^1$H-NMR spectrum (400 MHz): ($CDCl_3$, HMDSO) δ: 8.31 (d, J = 2.0 Hz, 1H), 7.79 (d, J = 9.2 Hz, 1H), 7.78 (dd, J = 8.7, 2.0 Hz, 1H), 7.71 (d, J = 8.7 Hz, 1H), 7.21 (dd, J = 9.2, 2.5 Hz, 1H), 6.87 (d, J = 2.5 Hz, 1H), 3.59 (dd, J = 6.9, 4.3 Hz, 1H), 3.21 (s, 3H), 3.12 (s, 6H), 2.96 (s, 3H), 2.68 (d, J = 4.3 Hz, 1H), 2.67 (d, J = 6.9 Hz, 1H); $^{13}$C-NMR spectrum (100 MHz): ($CDCl_3$, HMDSO) δ: 165.1, 150.6, 137.6, 130.4, 129.8, 128.5, 127.0, 124.4, 123.4, 117.0, 105.0, 40.3, 37.3, 36.0, 35.4, 32.3; LCMS ESI$^+$ (m/z): 348.1 $[M + H]^+$, LCMS purity 96.37% |
| C-3399 | Methyl 1-[[5-(dimethylamino)-2-naphthyl]sulfonyl]aziridine-2-carboxylate<br>Molecular formula: $C_{16}H_{18}N_2O_4S$; Molecular weight: 334.39; Melting point: 85-87° C.<br>$^1$H-NMR spectrum (400 MHz): (CDCl3, HMDSO) δ: 8.47 (d, J = 2.0 Hz, 1H), 8.40 (dt, J = 9.0, 0.7 Hz, 1H), 7.93 (dd, J = 9.0, 2.0 Hz, 1H), 7.63 (dt, J = 8.2, 1.0 Hz, 1H), 7.54 (dd, J = 8.2, 7.6 Hz, 1H), 7.25 (dd, J = 7.6, 1.0 Hz, 1H), 3.73 (s, 3H), 3.43 (dd, J = 7.1, 4.1 Hz, 1H), 2.90 (s, 6H), 2.84 (d, J = 7.1 Hz, 1H), 2.60 (d, J = 4.1 Hz, 1H); $^{13}$C-NMR spectrum (100 MHz): (CDCl3, HMDSO) δ: 167.2, 151.1, 133.6, 133.5, 131.1, 130.2, 127.8, 126.2, 123.9, 121.9, 117.4, 52.9, 45.1, 35.8, 32.1<br>LCMS ESI$^+$ (m/z): 335.1 $[M + H]^+$, LCMS purity 100% |
| C-3400 | 1-[[5-(Dimethylamino)-2-naphthyl]sulfonyl]-N,N-dimethylaziridine-2-carboxamide<br>Molecular formula: $C_{17}H_{21}N_3O_3S$; Molecular weight: 347.43; Melting point: 96-98° C.; $^1$H-NMR spectrum (400 MHz): ($CDCl_3$, HMDSO) δ: 8.47 (d, J = 1.9 Hz, 1H), 8.39 (dt, J = 9.0, 0.7 Hz, 1H), 7.94 (dd, J = 9.0, 1.9 Hz, 1H), 7.62 (dt, J = 8.2, 1.0 Hz, 1H), 7.53 (dd, J = 8.2, 7.6 Hz, 1H), 7.24 (dd, J = 7.6, 1.0 Hz, 1H), 3.67 (dd, J = 6.9, 4.3 Hz, 1H), 3.25 (s, 3H), 2.98 (s, 3H), 2.90 (s, 6H), 2.73 (d, J = 6.9 Hz, 1H), 2.72 (d, J = 4.3 Hz, 1H); $^{13}$C-NMR spectrum (100 MHz): ($CDCl_3$, HMDSO) δ: 167.9, 151.1, 133.9, 133.4, 131.0, 130.0, 127.8, 126.1, 123.8, 122.0, 117.3, 45.1, 37.3, 36.0, 35.3, 32.6; LCMS ESI$^+$ (m/z): 348.2 $[M + H]^+$, LCMS purity 100.00% |
| C-3402 | 1-(2,4-Difluorophenyl)sulfonylaziridine-2-carboxamide<br>Molecular formula: $C_9H_8F_2NO_3S$; Molecular weight: 262.23; Melting point: 141-143° C.; $^1$H-NMR spectrum (400 MHz): ($CDCl_3$, HMDSO) δ: 7.99 (dt, J = 8.5, 6.2 Hz, 1H), 7.87 (s, 1H), 7.66-7.74 (m, 1H), 7.47 (s, 1H), 7.36-7.43 (m, 1H), 3.38 (dd, J = 7.2, 4.5 Hz, 1H), 2.77 (d, J = 7.2 Hz, 1H), 2.59 (d, J = 4.5 Hz, 1H); $^{13}$C-NMR spectrum (100 MHz): ($CDCl_3$, HMDSO) δ: 166.6, 166.7 (dd, J = 256.9, 12.1 Hz,), 160.5 (dd, J = 258.8, 13.7 Hz,), 132.8 (d, J = 11.1 Hz,), 122.2 (dd, J = 14.6, 3.7 Hz,), 113.3 (dd, J = 22.4, 3.4 Hz,), 107.0 (t, J = 26.4 Hz,), 37.3, 32.3; LCMS ESI$^+$ (m/z): 263.1 $[M + H]^+$, LCMS purity 100.00% |
| C-3403 | 1-(2,4-Difluorophenyl)sulfonyl-N,N-dimethyl-aziridine-2-carboxamide<br>Molecular formula: $C_{11}H_{12}F_2NO_3S$; Molecular weight: 290.29; Melting point: oil; $^1$H-NMR spectrum (400 MHz): ($CDCl_3$, HMDSO) δ: 7.99 (ddd, J = 8.8, 7.8, 6.0 Hz, 1H), 6.96-7.06 (m, 2H), 3.26 (s, 3H), 2.99 (s, 3H), 3.71 (dd, J = 7.0, 4.4 Hz, 1H), 2.88 (d, J = 7.0 Hz, 1H), 2.81 (d, J = 4.4 Hz, 1H); $^{13}$C-NMR spectrum (100 MHz): ($CDCl_3$, HMDSO) δ: 166.7 (dd, J = 259.4, 11.6 Hz,), 164.5, 160.5 (dd, J = 260.8, 13.1 Hz,), 132.3 (d, J = 10.9 Hz,), 122.3 (dd, J = 14.6, 3.8 Hz,), 112.1 (dd, J = 22.2, 3.4 Hz,), 106.0 (t, J = 25.6 Hz,), 37.2, 36.1, 35.1, 33.4; LCMS ESI$^+$ (m/z): 291.1 $[M + H]^+$, LCMS purity 94.31% |
| C-3427 | Methyl 1-[[8-(dimethylamino)-2-naphthyl]sulfonyl]aziridine-2-carboxylate<br>Molecular formula: $C_{16}H_{18}N_2O_4S$; Molecular weight: 334.39; Melting point: oil;<br>$^1$H-NMR spectrum (400 MHz): ($CDCl_3$, HMDSO) δ: 8.88-8.89 (m, 1H), 7.96 (dd, J = 8.8, 0.7 Hz, 1H), 7.92 (dd, J = 8.8, 1.8 Hz, 1H), 7.58 (dd, J = 8.2, 6.7 Hz, 1H), 7.55 (ddd, J = 8.2, 1.8, 0.7 Hz, 1H), 7.17 (dd, J = 6.7, 1.8 Hz, 1H), 3.72 (s, 3H), 3.42 (dd, J = 7.1, 4.1 Hz, 1H), 2.92 (s, 6H), 2.84 (d, J = 7.1 Hz, 1H), 2.59 (d, J = 4.1 Hz, 1H); $^{13}$C-NMR spectrum (100 MHz): ($CDCl_3$, HMDSO) δ: 167.2, 152.6, 137.1, 132.8, 129.9, 129.7, 127.6, 126.8, 122.8, 122.2, 115.7, 52.8, 45.2, 35.8, 32.1; LCMS ESI$^+$ (m/z): 335.2 $[M + H]^+$, LCMS purity 100.00% |
| C-3459 | 1-[[6-(Dimethylamino)-1-naphthyl]sulfonyl]aziridine-2-carboxamide<br>Molecular formula: $C_{15}H_{17}N_3O_3S$; Molecular weight: 319.38; Melting point: 197-199° C.<br>$^1$H-NMR spectrum (300 MHz): (DMSO-$D_6$, HMDSO) δ: 8.55 (d, J = 9.6 Hz, 1H), 8.07 (d, J = 8.3 Hz, 1H), 7.80 (dd, J = 7.3, 1.0 Hz, 1H), 7.76 (br s, 1H), 7.51 (dd, J = 8.3, 7.3 Hz, 1H), 7.45 (dd, J = 9.6, 2.7 Hz, 1H), 7.37 (br s, 1H), 7.11 (d, J = 2.7 Hz, 1H), 3.28-3.38 (m, overlapped with water, 1H), 3.09 (s, 6H), 2.68 (d, J = 7.2 Hz, 1H), 2.47 (d, J = 4.4 Hz, 1H); $^{13}$C-NMR spectrum (100 MHz): (DMSO-$D_6$, HMDSO) δ: 171.8, 154.0, 141.2, 138.8, 137.3, 130.9, 130.0, 129.7, 125.7, 123.3, 111.3, 45.8, 41.2, 36.9; LCMS ESI$^+$ (m/z): 320.3 $[M + H]^+$, LCMS purity 100% |
| C-3511 | [1-(4-Hexylphenyl)sulfonylaziridin-2-yl]-pyrrolidin-1-yl-methanone<br>Molecular formula: $C_{19}H_{28}N_2O_3S$; Molecular weight: 364.50; Melting point: oil<br>$^1$H-NMR spectrum (400 MHz): ($CDCl_3$, HMDSO) δ: 7.85 (d, J = 8.3 Hz, 2H), 7.34 (d, J = 8.3 Hz, 2H), 3.75 (dt, J = 10.1, 6.7 Hz, 1H), 3.63 (dt, J = 10.1, 7.0 Hz, 1H), 3.42-3.54 (m, 3H), 2.70 (d, J = 4.2 Hz, 1H), 2.68 (t, J = 7.9 Hz, 2H), 2.64 (d, J = 6.9 Hz, 1H), 1.93-2.05 (m, 2H), 1.81-1.93 (m, 2H), 1.57-1.69 (m, 2H), 1.23-1.38 (m, 6H), 0.88 (t, J = 7.0 Hz, 3H); $^{13}$C-NMR spectrum (100 MHz): ($CDCl_3$, HMDSO) δ: 163.4, 150.0, 134.4, 129.2, 128.3, 46.8, 46.5, 36.0, 35.8, 32.4, 31.6, 31.0, 28.9, 26.1, 24.2, 22.6, 14.1; LCMS ESI$^+$ (m/z): 365.3 $[M + H]^+$, LCMS purity 100% |
| C-3517 | [1-(4-Hexylphenyl)sulfonylaziridin-2-yl]-morpholino-methanone<br>Molecular formula: $C_{19}H_{28}N_2O_4S$; Molecular weight: 380.18; Melting point: oil<br>$^1$H-NMR spectrum (400 MHz): ($CDCl_3$, HMDSO) δ: 7.85 (d, J = 8.4 Hz, 2H), 7.36 (d, J = 8.4 Hz, 2H), 3.75-3.86 (m, 2H), 3.57-3.75 (m, 5H), 3.55 (dd, J = 6.8, 4.2 Hz, 1H), 3.46 (ddd, J = 13.3, 7.7, 3.3 Hz, 1H), 2.71 (d, J = 4.2 Hz, 1H), 2.69 (t, J = 7.9 Hz, 2H), 2.67 (d, J = 6.8 Hz, 1H), 1.57-1.68 (m, 2H), 1.23-1.39 (m, 6H), 0.88 (t, J = 7.0 Hz, 3H); $^{13}$C-NMR spectrum (100 MHz): ($CDCl_3$, HMDSO) δ: 163.7, 150.3, 134.3, 129.3, 128.2, 66.7, 66.6, 42.8, 36.0, 35.3, 32.4, 31.6, 31.0, 28.9, 22.7, 14.1; LCMS ESI$^+$ (m/z): 381.3 $[M + H]^+$, LCMS purity 100% |
| C-3520 | [1-(4-hexylphenyl)sulfonylaziridin-2-yl]-(1-piperidyl)methanone<br>Molecular formula: $C_{20}H_{30}N_2O_3S$; Molecular weight: 378.53; Melting point: oil<br>$^1$H-NMR spectrum (400 MHz): ($CDCl_3$, HMDSO) δ: 7.86 (d, J = 8.4 Hz, 2H), 7.35 (d, J = 8.4 Hz, 2H), 3.62-3.73 (m, 2H), 3.54 (dd, J = 6.8, 4.2 Hz, 1H), 3.52-3.60 (m, 1H), 3.38-3.46 (m, 1H), 2.69 (t, J = 7.3 Hz, 2H), 2.70 (d, J = 4.2 Hz, 1H), 2.66 (d, J = 6.8 Hz, 1H), 1.60-1.70 (m, 4H), 1.49- |

TABLE 1-continued

| | |
|---|---|
| | 1.60 (m, 4H), 1.24-1.38 (m, 6H), 0.88 (t, J = 7.0 Hz, 3H); $^{13}$C-NMR spectrum (100 MHz): ($CDCl_3$, HMDSO) δ: 163.3, 150.0, 134.6, 129.2, 128.2, 46.9, 43.6, 36.0, 35.7, 32.3, 31.6, 31.0, 28.9, 26.4, 25.4, 24.4, 22.6, 14.1; LCMS ESI$^+$ (m/z): 379.3 $[M + H]^+$, LCMS purity 100% |
| C-3532 | 1-(Benzenesulfonyl)aziridine-2-carboxamide<br>Molecular formula: $C_9H_{10}N_2O_3S$; Molecular weight: 226.25; Melting point: 108-110° C. $^1$H-NMR spectrum (400 MHz): ($CDCl_3$, HMDSO) δ: 7.93-7.98 (m, 2H), 7.67-7.73 (m, 1H), 7.55-7.63 (m, 2H), 6.11 (s, 1H), 5.82 (s, 1H), 3.28 (dd, J = 7.7, 4.2 Hz, 1H), 2.81 (d, J = 7.7 Hz, 1H), 2.45 (d, J = 4.2 Hz, 1H); $^{13}$C-NMR spectrum (100 MHz): ($CDCl_3$, HMDSO) δ: 168.3, 136.6, 134.4, 129.5, 128.2, 37.7, 33.2; LCMS ESI$^+$ (m/z): 227.2 $[M + H]^+$, LCMS purity 100.00% |
| C-3535 | Methyl (2S)-1-(p-tolylsulfonyl)aziridine-2-carboxylate<br>Molecular formula: $C_{11}H_{13}NO_4S$; Molecular weight: 255.29. Melting point: oil. $^1$H-NMR spectrum (400 MHz): ($CDCl_3$, HMDSO) δ: 7.84 (d, J = 8.3 Hz, 2H), 7.36 (d, J = 8.3 Hz, 2H), 3.74 (s, 3H), 3.34 (dd, J = 7.1, 4.1 Hz, 1H), 2.76 (d, J = 7.1 Hz, 1H), 2.56 (d, J = 4.1 Hz, 1H), 2.45 (s, 3H). $^{13}$C-NMR spectrum (100 MHz ($CDCl_3$, HMDSO) δ: 167.2, 145.3, 134.0, 129.9, 128.2, 52.9, 35.7, 32.0, 21.7. LCMS ESI$^+$ (m/z): 256.1 $[M + H]^+$, LCMS purity 100% |
| C-3537 | Ethyl 1-(p-tolylsulfonyl)aziridine-2-carboxylate<br>Molecular formula: $C_{12}H_{15}NO_4S$. Molecular weight: 269.32. Melting point: oil. $^1$H-NMR spectrum (400 MHz): ($CDCl_3$, HMDSO) δ: 7.85 (d, J = 8.3 Hz, 2H), 7.35 (d, J = 8.3 Hz, 2H), 4.12-4.24 (m, 2H), 3.32 (dd, J = 7.1, 4.1 Hz, 1H), 2.75 (d, J = 7.1 Hz, 1H), 2.55 (d, J = 4.1 Hz, 1H), 2.45 (s, 3H), 1.25 (t, J = 7.1 Hz, 3H). $^{13}$C-NMR spectrum (100 MHz ($CDCl_3$, HMDSO) δ: 166.8, 145.2, 134.1, 130.0, 128.3, 62.1, 35.9, 32.0, 21.7, 14.0. LCMS ESI$^+$ (m/z): 270.2 $[M + H]^+$, LCMS purity 100% |
| C-3539 | Methyl (2R)-1-(p-tolylsulfonyl)aziridine-2-carboxylate<br>Molecular formula: $C_{11}H_{13}NO_4S$; Molecular weight: 255.29. Melting point: oil. $^1$H-NMR spectrum (400 MHz): ($CDCl_3$, HMDSO) δ: 7.84 (d, J = 8.3 Hz, 2H), 7.36 (d, J = 8.3 Hz, 2H), 3.74 (s, 3H), 3.34 (dd, J = 7.1, 4.1 Hz, 1H), 2.76 (d, J = 7.1 Hz, 1H), 2.56 (d, J = 4.1 Hz, 1H), 2.45 (s, 3H). $^{13}$C-NMR spectrum (100 MHz ($CDCl_3$, HMDSO) δ: 167.2, 145.3, 134.0, 129.9, 128.2, 52.9, 35.7, 32.0, 21.7. LCMS ESI$^+$ (m/z): 256.1 $[M + H]^+$, LCMS purity 100%. $^{13}$C-NMR spectrum (100 MHz ($CDCl_3$, HMDSO) δ: 167.3, 145.3, 134.0, 130.0, 128.3, 53.0, 35.7, 32.1, 21.7. LCMS ESI$^+$ (m/z): 256.1 $[M + H]^+$, LCMS purity 97.75% |
| C-3546 | N,N-Diethyl-1-(4-hexylphenyl)sulfonyl-aziridine-2-carboxamide<br>Molecular formula: $C_{19}H_{30}N_2O_3S$; Molecular weight: 366.52; Melting point: oil<br>$^1$H-NMR spectrum (400 MHz): ($CDCl_3$, HMDSO) δ: 7.86 (d, J = 8.4 Hz, 2H), 7.34 (d, J = 8.4 Hz, 2H), 3.56 (dq, J = 15.0, 7.2 Hz, 1H), 3.54 (dd, J = 6.8, 4.2 Hz, 1H), 3.49 (dq, J = 15.0, 7.2 Hz, 1H), 3.32-3.44 (m, 2H), 2.69 (d, J = 4.2 Hz, 1H), 2.69 (t, J = 7.9 Hz, 2H), 2.65 (d, J = 6.9 Hz, 1H), 1.56-1.67 (m, 2H), 1.26-1.38 (m, 6H), 1.26 (t, J = 7.2 Hz, 3H), 1.13 (t, J = 7.2 Hz, 3H), 0.89 (t, J = 7.0 Hz, 3H); $^{13}$C-NMR spectrum (100 MHz): ($CDCl_3$, HMDSO) δ: 164.3, 150.0, 134.5, 129.2, 128.2, 42.1, 41.1, 36.0, 34.9, 32.5, 31.6, 31.0, 28.8, 22.6, 14.7, 14.1, 12.8; LCMS ESI$^+$ (m/z): 367.3 $[M + H]^+$, LCMS purity 100% |
| C-3548 | Methyl (2S)-1-[[6-(dimethylamino)-1-naphthyl]sulfonyl]aziridine-2-carboxylate<br>Molecular formula: $C_{16}H_{18}N_2O_4S$; Molecular weight: 334.39; Melting point: 118-120° C.<br>$^1$H-NMR spectrum (400 MHz): ($CDCl_3$, HMDSO) δ: 8.73 (d, J = 9.6 Hz, 1H), 7.91 (d, J = 8.3 Hz, 1H), 7.87 (dd, J = 7.3, 1.2 Hz, 1H), 7.39 (dd, J = 8.3, 7.4 Hz, 1H), 7.33 (dd, J = 9.6, 2.7 Hz, 1H), 6.93 (d, J = 2.7 Hz, 1H), 3.70 (s, 3H), 3.44 (dd, J = 7.1, 4.1 Hz, 1H),), 3.08 (s, 6H), 2.83 (d, J = 7.1 Hz, 1H), 2.55 (d, J = 4.2 Hz, 1H); $^{13}$C-NMR spectrum (100 MHz): ($CDCl_3$, HMDSO) δ: 167.3, 148.9, 136.2, 133.8, 132.0, 126.2, 125.6, 124.1, 121.5, 118.2, 106.2, 52.8, 40.4, 35.7, 32.3. LCMS ESI$^+$ (m/z): 335.2 $[M + H]^+$, LCMS purity 100% |
| C-3559 | Methyl 1-(3-pyridylsulfonyl)aziridine-2-carboxylate<br>Molecular formula: $C_9H_{10}N_2O_4S$; Molecular weight: 242.25; Melting point: oil<br>$^1$H-NMR spectrum (400 MHz): ($CDCl_3$, HMDSO) δ: 9.17 (dd, J = 2.3, 0.7 Hz, 1H), 8.90 (dd, J = 4.9, 1.6 Hz, 1H), 8.28 (ddd, J = 8.1, 2.3, 1.7 Hz, 1H), 7.53 (ddd, J = 8.1, 4.9, 0.7 Hz, 1H), 3.76 (s, 3H), 3.45 (dd, J = 7.1, 4.2 Hz, 1H), 2.87 (d, J = 7.1 Hz, 1H), 2.65 (d, J = 4.2 Hz, 1H); $^{13}$C-NMR spectrum (100 MHz): ($CDCl_3$, HMDSO) δ: 166.88, 154.7, 148.8, 135.9, 134.2, 124.1, 53.1, 36.0, 32.4; LCMS ESI$^+$ (m/z): 243.1 $[M + H]^+$, LCMS purity 92.21% |
| C-3562 | 1-(3-pyridylsulfonyl)aziridine-2-carboxamide<br>Molecular formula: $C_8H_9N_3O_3S$; Molecular weight: 227.24; Melting point: 147-149° C.<br>$^1$H-NMR spectrum (400 MHz): (DMSO-$D_6$, HMDSO) δ: 9.11 (dd, J = 2.3, 0.7 Hz, 1H), 8.96 (dd, J = 4.9, 1.6 Hz, 1H), 8.38 (ddd, J = 8.1, 2.3, 1.6 Hz, 1H), 7.87 (s, 1H), 7.53 (ddd, J = 8.1, 4.9, 0.7 Hz, 1H), 7.46 (s, 1H), 3.34-3.38 (m, 1H, overlapped with $H_2O$), 2.77 (d, J = 7.2 Hz, 1H), 2.56 (d, J = 4.5 Hz, 1H); $^{13}$C-NMR spectrum (100 MHz): (DMSO-$D_6$, HMDSO) δ: 166.69, 155.3, 148.5, 136.4, 134.1, 125.1, 37.6, 32.0; LCMS ESI$^+$ (m/z): 228.1 $[M + H]^+$, LCMS purity 100% |
| C-3570 | Methyl (2R)-1-[[6-(dimethylamino)-1-naphthyl]sulfonyl]aziridine-2-carboxylate<br>Molecular formula: $C_{16}H_{18}N_2O_4S$; Molecular weight: 334.39; Melting point: 117-119° C.<br>$^1$H-NMR spectrum (400 MHz): ($CDCl_3$, HMDSO) δ: 8.73 (d, J = 9.5 Hz, 1H), 7.91 (d, J = 8.3 Hz, 1H), 7.87 (dd, J = 7.3, 1.2 Hz, 1H), 7.39 (dd, J = 8.3, 7.4 Hz, 1H), 7.33 (dd, J = 9.5, 2.7 Hz, 1H), 6.93 (d, J = 2.7 Hz, 1H), 3.70 (s, 3H), 3.44 (dd, J = 7.1, 4.1 Hz, 1H),), 3.08 (s, 6H), 2.83 (d, J = 7.1 Hz, 1H), 2.55 (d, J = 4.2 Hz, 1H); $^{13}$C-NMR spectrum (100 MHz): ($CDCl_3$, HMDSO) δ: 167.4, 148.9, 136.3, 133.8, 132.0, 126.2, 125.6, 124.2, 121.6, 118.2, 106.3, 52.8, 40.4, 35.7, 32.4; LCMS ESI$^+$ (m/z): 335.3 $[M + H]^+$, LCMS purity 100% |
| C-3576 | Methyl 1-(4-fluorophenyl)sulfonylaziridine-2-carboxylate<br>Molecular formula: $C_{10}H_{10}FNO_4S$; Molecular weight: 259.25; Melting point: oil<br>$^1$H-NMR spectrum (400 MHz): ($CDCl_3$, HMDSO) δ: 7.96-8.02 (m, 2H), 7.21-7.27 (m, 2H), 3.74 (s, 3H), 3.37 (dd, J = 7.1, 4.1 Hz, 1H), 2.79 (d, J = 7.1 Hz, 1H), 2.59 (d, J = 4.1 Hz, 1H); $^{13}$C-NMR spectrum (100 MHz): ($CDCl_3$, HMDSO) δ: 167.1, 166.1 (d, J = 257.1 Hz, 1H), 133.2 (d, J = 3.1 Hz, 1H), 131.1 (d, J = 9.9 Hz, 1H), 116.7 (d, J = 22.9 Hz, 1H), 53.0, 35.9, 32.2; LCMS ESI$^+$ (m/z): 260.2 $[M + H]^+$, LCMS purity 100% |
| C-3591 | 1-(4-tert-Butylphenyl)sulfonylaziridine-2-carboxamide<br>Molecular formula: $C_{13}H_{18}N_2O_3S$. Molecular weight: 282.36. Melting point: 151-153° C. $^1$H-NMR spectrum (400 MHz): ($CDCl_3$, HMDSO) δ: 7.86 (d, J = 8.8 Hz, 2H), 7.59 (d, J = 8.8 Hz, 2H), 6.07 (br s, 1H), 5.42 (br s, 1H), 3.24 (dd, J = 7.7, 4.2 Hz, 1H), 2.81 (d, J = 7.7 Hz, 1H), 2.44 |

TABLE 1-continued

| | |
|---|---|
| | (d, J = 4.2 Hz, 1H), 1.36 (s, 9H). $^{13}$C-NMR spectrum (100 MHz (CDCl$_3$, HMDSO) δ: 168.4, 158.5, 133.2, 128.1, 126.5, 37.6, 35.4, 33.2, 31.4. LCMS ESI$^+$ (m/z): 283.3 [M + H]$^+$, LCMS purity 100% |
| C-3593 | 1-(4-tert-Butylphenyl)sulfonyl-N-methylaziridine-2-carboxamide<br>Molecular formula: $C_{14}H_{20}N_2O_3S$. Molecular weight: 296.38. Melting point: 146-148° C. $^1$H-NMR spectrum (400 MHz): (CDCl$_3$, HMDSO) δ: 7.85 (d, J = 8.7 Hz, 2H), 7.59 (d, J = 8.7 Hz, 2H), 6.16 (br s, 1H), 3.28 (dd, J = 7.7. 4.2 Hz, 1H), 2.76 (d, J = 4.9 Hz, 3H), 2.73 (d, J = 7.7 Hz, 1H), 2.36 (d, J = 4.2 Hz, 1H), 1.36 (s, 9H). $^{13}$C-NMR spectrum (100 MHz (CDCl$_3$, HMDSO) δ: 166.3, 158.5, 133.1, 128.2, 126.5, 37.9, 35.4, 33.5, 31.0, 26.0. LCMS ESI$^+$ (m/z): 297.3 [M + H]$^+$, LCMS purity 100% |
| C-3594 | 1-(4-tert-Butylphenyl)sulfonyl-N,N-dimethyl-aziridine-2-carboxamide<br>Molecular formula: $C_{15}H_{22}N_2O_3S$. Molecular weight: 310.41. Melting point: 104-106° C. $^1$H-NMR spectrum (400 MHz): (CDCl$_3$, HMDSO) δ: 7.88 (d, J = 8.6 Hz, 2H), 7.56 (d, J = 8.6 Hz, 2H), 3.23 (s, 3H), 3.60 (dd, J = 6.8, 4.2 Hz, 1H), 3.23 (s, 3H), 2.98 (s, 3H), 2.69 (d, J = 6.8 Hz, 1H), 2.66 (d, J = 4.2 Hz, 1H), 1.35 (s, 9H). $^{13}$C-NMR spectrum (100 MHz (CDCl$_3$, HMDSO) δ: 165.0, 159.1, 134.2, 128.0, 126.3, 37.3, 36.0, 35.3, 35.2, 31.1. LCMS ESI$^+$ (m/z): 311.3 [M + H]$^+$, LCMS purity 100% |
| C-3612 | Lithium 1-tosylaziridine-2-carboxylate<br>Molecular formula: $C_{10}H_{10}LiNO_4S$; Molecular weight: 247.20; Melting point: 222-224° C. (decomp.); $^1$H-NMR spectrum (400 MHz): (D$_2$O, HMDSO) d: 7.84 (d, J = 8.3 Hz, 2H), 7.49 (d, J = 8.3 Hz, 2H), 3.10 (dd, J = 7.1, 4.1 Hz, 1H), 2.74 (d, J = 7.1 Hz, 1H), 2.51 (d, J = 4.1 Hz, 1H), 2.44 (s, 3H); $^{13}$C-NMR spectrum (100 MHz): (D$_2$O, HMDSO) d: 173.2, 146.7, 131.6, 130.2, 127.9, 39.0, 32.3, 20.8. LCMS ESI$^-$ (m/z): 240.2 [M − Li]$^-$, LCMS purity 95.83% |

EXAMPLE 2. INHIBITION OF PDI A3

The inhibitory effects compounds of invention on activity of PDIA3 was assess based on the insulin turbidimetric assay. Enzymatic activity of PDIA3 was confirmed by measuring the turbidity increase at 650 nm due to insulin reduction. The assay mixture was prepared by addition 10 ug/ml PDI A3 (*E. coli* recombinant protein; Mybiosource), 0.1 mM phosphate buffer (pH7.6), 1 mM EDTA, 0.087 mM DTT and with or without tested compound and was incubated for 60 min, at 37° C. Reaction was started by addition of insulin and DTT. Final concentration of insulin and DTT in assay mixture were 0.15 mMv and 0.174 mMv, respectively. Turbidity was detected at 650 nm against reference samples without PDJs. The measurements were performed at 650 nm using 120-s recordings. The table 2 shows the results of the PDI A3 inhibition by disclosed compounds.

TABLE 2

Inhibition of PDI A3

| Compound Number | Inhibition of PDI A3 (EC 50, [μM) | Compound Number | Inhibition of PDI A3 (EC 50, [μM) | Compound Number | Inhibition of PDI A3 (EC 50, [μM) |
|---|---|---|---|---|---|
| C-3376 | 2.8 | C-3314 | 24.0 | C-3355 | 61.0 |
| C-3399 | 4.0 | C-3364 | 24.0 | C-3294 | 68.0 |
| C-3390 | 4.0 | C-3403 | 24.0 | C-3320 | 69.0 |
| C-3375 | 4.3 | C-3393 | 27.0 | C-3570 | 68.4 |
| C-3377 | 4.3 | C-3161 | 27.0 | C-3291 | 77.0 |
| C-3548 | 5.3 | C-3316 | 28.0 | C-3295 | 78.0 |
| C-3373 | 5.4 | C-3576 | 28.0 | C-3326 | 84.0 |
| C-3400 | 6.7 | C-3290 | 29.0 | C-3336 | 89.0 |
| C-3520 | 6.7 | C-3591 | 29.0 | C-3365 | 90.0 |
| C-3535 | 6.8 | C-3537 | 30.0 | C-3311 | 90.0 |
| C-3371 | 7.5 | C-3212 | 32.0 | C-3263 | 98.0 |
| C-3391 | 7.6 | C-3594 | 32.0 | C-3511 | 102.0 |
| C-3397 | 8.5 | C-3332 | 35.0 | C-3292 | 114.0 |
| C-3532 | 9.3 | C-3380 | 37.0 | C-3287 | 122.0 |
| C-3383 | 10.1 | C-3327 | 37.0 | C-3342 | 123.0 |
| C-3427 | 10.5 | C-3366 | 37.0 | C-3459 | 130.0 |
| C-3398 | 10.5 | C-3308 | 40.0 | C-3319 | 145.0 |
| C-3385 | 11.1 | C-3374 | 40.0 | C-3353 | 143.0 |
| C-3384 | 11.7 | C-3272 | 43.0 | C-3304 | 190.0 |
| C-3343 | 14.0 | C-3216 | 48.0 | C-3357 | >200 |
| C-3517 | 14.7 | C-3257 | 48.0 | C-3305 | >200 |
| C-3369 | 18.0 | C-3299 | 48.0 | C-3256 | >200 |

TABLE 2-continued

Inhibition of PDI A3

| Compound Number | Inhibition of PDI A3 (EC 50, [μM) | Compound Number | Inhibition of PDI A3 (EC 50, [μM) | Compound Number | Inhibition of PDI A3 (EC 50, [μM) |
|---|---|---|---|---|---|
| C-3559 | 18.6 | C-3350 | 48.0 | C-3270 | >200 |
| C-3362 | 19.4 | C-3271 | 52.5 | C-3281 | >200 |
| C-3220 | 22.0 | C-3251 | 52.5 | C-3297 | >200 |
| C-3389 | 23.3 | C-3562 | 56.0 | C-3303 | >200 |
| C-3368 | 24.0 | | | | |

EXAMPLE 3. EVALUATION OF ANTI-AGGREGATORY EFFECT OF PDI A3 INHIBITORS IN VITRO AND THEIR ANTI-THROMBOTIC EFFECTS IN VIVO

Anti-platelet activity of compounds of invention was assessed using light transmission aggregometry assay of human platelet-rich plasma (PRP). Venous blood was obtained from male volunteers at the University Hospital Blood Bank Centre. Volunteer donors had not taken any medicines for the preceding two weeks. Blood was collected into vials containing sodium citrate (3.2%, 9:1 v/v) as an anti-coagulant agent. To obtain platelet rich plasma (PRP), blood was centrifuged at 260×g for 15 min. The platelet pure plasma fraction (used as a blank sample) was obtained by centrifugation of the remaining blood for 10 min at 2600×g. Aggregation of blood platelets was assessed in PRP with a dual channel Chronolog aggregometer (CHRONO-LOG) using a method previously described by Born[35]. PRP (500 μl) was equilibrated for 2 min at 37° C. with a continuous stirring at 800 rpm and then stimulated with collagen to cause aggregation. At the beginning of each experiment, concentrations of collagen that induced sub-maximum aggregation response were determined. These concentrations were in the range of 1-5 mg/ml, respectively. All the tested compounds were added 2 min prior to stimulation of platelets with collagen. Transmittance was read 6 min after stimulation of platelets with an agonist. FIG. 1 present shows inhibition of aggregation of human platelets by reference PDI inhibitors; while FIG. 2, 3 show inhibition of aggregation of human platelets by PDI A3 inhibitors of the invention.

As shown on FIG. 1, inhibition of platelet aggregation by reference PDI inhibitors in human PRP (Bepristat, LOC-14, CCF642 and rutin trihydrate) was tested. Data represent the means±SD of at least two independent experiments; n=2-8 replicates in each experiment.

Figure 2:
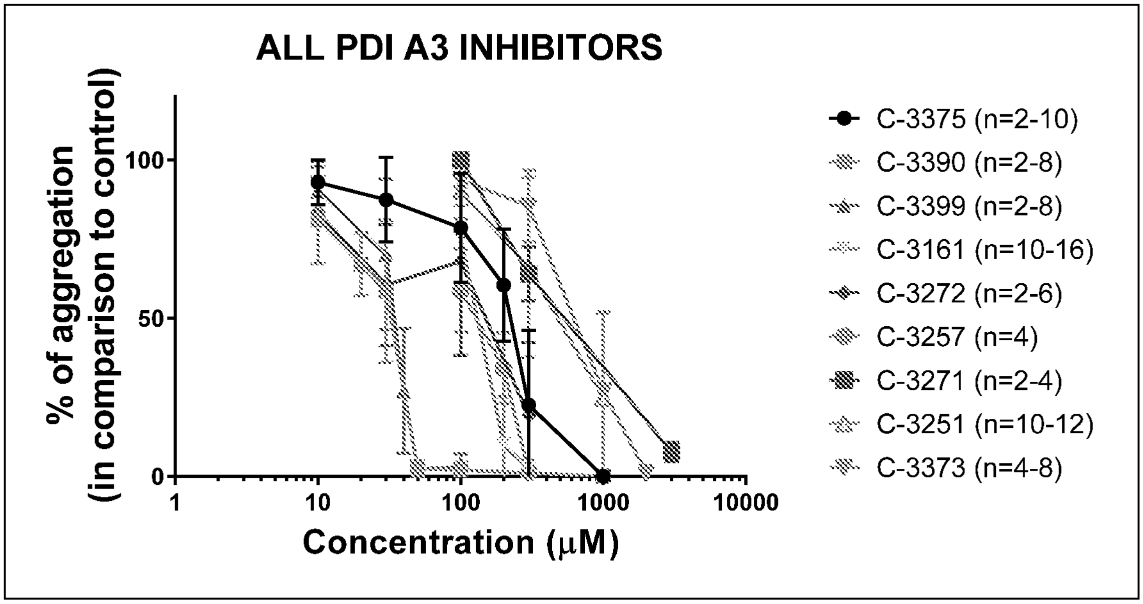
FIG. 2, 3 show inhibition of aggregation of human platelets by PDI A3 inhibitors of the invention.
Figure 3:
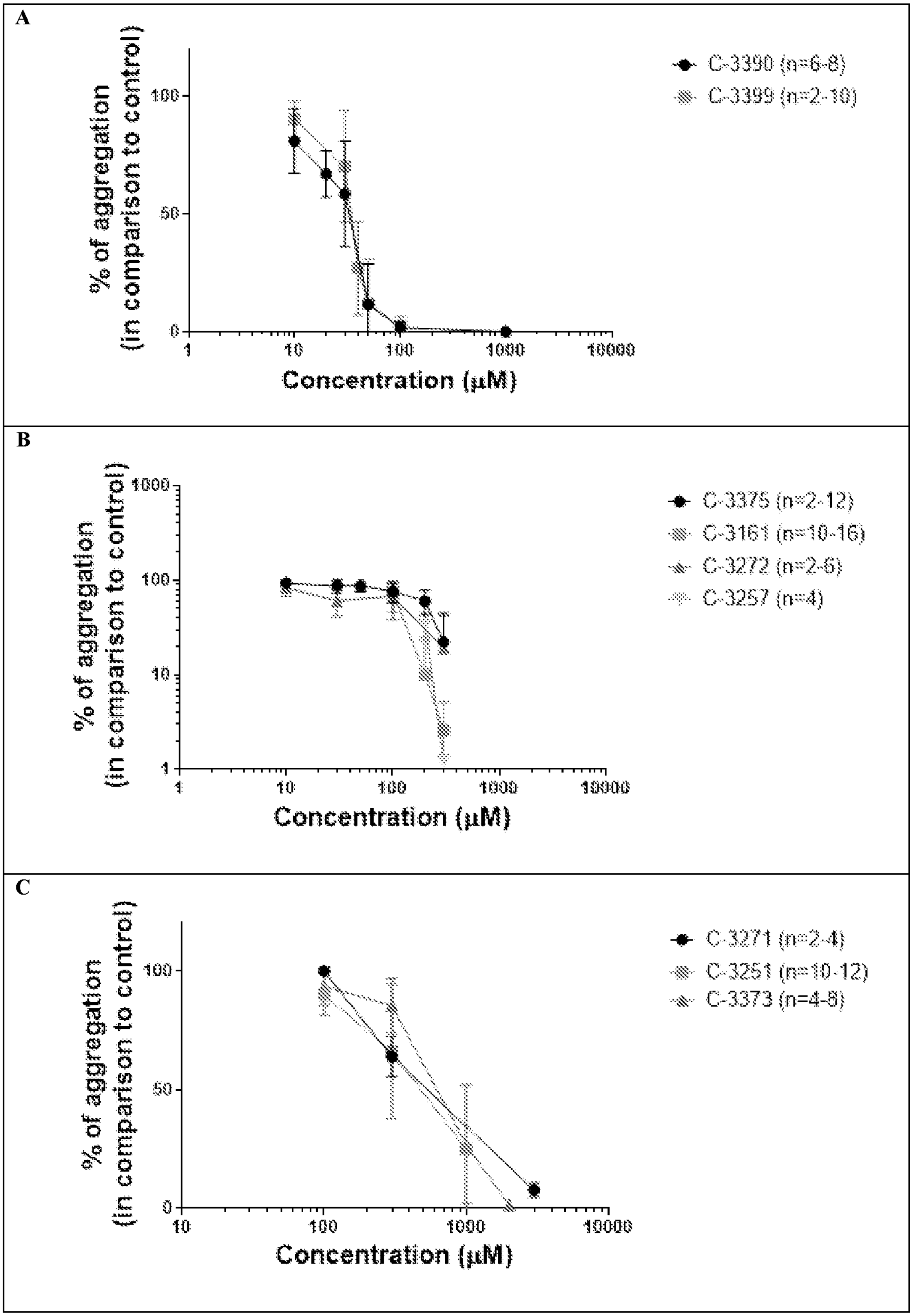

FIG. 2 shows inhibition of platelet aggregation by 7 tested compounds among PDI A3 inhibitors according to invention. Experiments were performed in human PRP, data are shown in comparison to control; data represent the means±SD of at least two independent experiments; n=2-10 replicates in each experiment. The most promising compounds seem to be C-3390 and C-3399: as these two compounds have the lowest EC50 and their antiplatelet effects is shown on FIG. 3A. The other compounds have a lower potency, but all of them have a dose-dependent inhibitory effect on platelet aggregation in human platelet rich plasma as shown in FIGS. 3B and 3C.

Figures 4, 5:
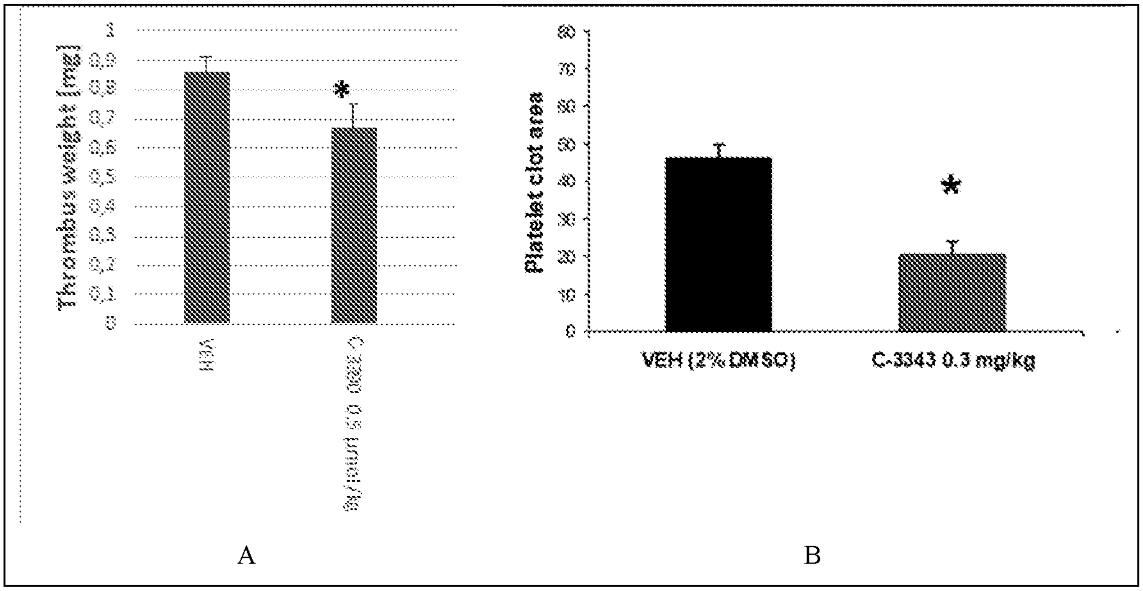
FIG. 4 shows correlation between the inhibition of the PDI A3 and the inhibition of platelet aggregation for PDI A3 inhibitors of the invention.
FIG. 5 shows antiplatelet antithrombotic effects in in vivo model of thrombosis for selected PDI-inhibitor and reference compounds.

As shown of FIG. 4, there was a significant correlation between inhibiting PDI A3 (EC50) of selected PDI A3 inhibitors and theirs inhibitory effect on platelet aggregation (in 100 μM concentration). Experiments were performed in human PRP, data represent the means of at least two independent experiments; n=2-10 replicates in each experiment. These results support strongly the notion that inhibitory effects on platelet aggregation of compounds of invention is related to the inhibition of PDI A3.

To confirm antithrombotic activity of compounds of invention, inhibitors of PDIA3, pharmacological activity of selected compounds was tested in vivo in the rat or mice model of arterial thrombosis. Wistar rats were anaesthetized with pentobarbital (40 mg/kg, i.p.) and placed in a supine position on a heated (37° C.) operating table. Arterial thrombosis was induced by electrical stimulation of the right common carotid artery, as previously described (Kramkowski et al., 2012). Briefly, the anode, a stainless steel L-shaped wire, was inserted under the artery and connected to a constant current generator. The cathode was attached subcutaneously to the hind limb. The artery was stimulated (1 mA) for 10 min. Fifty-five minutes after the beginning of stimulation, the segment of the common carotid artery containing the formed thrombus was dissected and opened lengthwise, and the thrombus was completely removed and air-dried at room temperature for 24 h. Thrombus was then weighed in a blinded manner. Antithrombotic effects of compounds of invention in mice was analyzed using intravital fluorescence confocal microscopy as described previously (Hayashi T et al., 2008). GFP mice were anesthetized with pentobarbital (50 mg/kg, i.p.) a midline laparotomy incision was made, and then the mesentery of the ileum was pulled out of the abdomen and draped over a plastic mound. The mesentery was continuously perfused with 37° C.-warmed saline to prevent the vessels from drying. Mesenteric vessels were identified and endothelial injury was induced by a 514-nm argon-ion laser. For visualizing the surface-exposed platelet phospholipids in a thrombus, Alexa Fluor 568-labeled annexin V (ANX; 2-μg/g mouse body weight) was administered into the right femoral vein 14 minutes before laser injury. Changes in fluorescence intensity were measured as described previously (Hayashi T et al., 2008, Kramkowski et al., 2002)

FIG. 5 shows anti-thrombotic effects of C3990 and C-3343 two chosen compounds of invention in in vivo models of arterial thrombosis.

EXAMPLE 4. THE IN VITRO ANTIPROLIFERATIVE EFFECT OF PDI A3 INHIBITORS TOWARDS PANEL OF CANCER CELLS (48-HOUR EXPOSITION)

Anticancer activity of compounds of invention, PDI A3-inhibitors has been tested in vitro in classical antiproliferative assay in various cancer cells lines. Monolayer tumor cell lines MDA-MB-231 (human mammary breast adenocarcinoma), MCF-7 (human breast adenocarcinoma, estrogen-positive), HT-1080 (human fibrosarcoma) and Caco-2 (human colon adenocarcinoma) were cultured in standard medium DMEM (Dulbecco's modified Eagle's medium) ("Sigma") supplemented with 10% foetal bovine serum ("Sigma"). About 2000-4000 cells per well (depending on line nature) were placed in 96-well plates and after 24 h compounds were added to the wells. Untreated cells were used as a control. The plates were incubated for 48 h, 37° C., 5% $CO_2$. The number of surviving cells was determined using 3-(4,5-dimethylthiazol-2-yl)-2,5-diphenyltetrazolinium bromide (MTT). MTT-test: after incubating culture medium was removed and 200 μL fresh medium with 20 μL MTT (2 mg/mL in HBSS) was added in each well of the plate. After incubation (3 hr., 37° C., 5% $CO_2$), the medium with MTT was removed and 200 μL DMSO were added at once to each sample. The samples were tested at 540 nm on Thermo Scientific Multiskan EX microplate photometer. The half-maximal inhibitory concentration ($IC_{50}$) of each compound was calculated using Graph Pad Prism® 3.0. The results are presented in Table 5.

TABLE 5

The in vitro antiproliferative effect of PDI A3 inhibitors towards panel of cancer cells (48-hour exposition)

| | Cytotoxicity, IC50, μM | | | |
|---|---|---|---|---|
| Comp. | HT-1080 | CaCo-2 | MDA-MB-231 | MCF-7 |
| C-3212 | 56 ± 9 | 45 ± 4 | 46 ± 8 | 54 ± 4 |
| C-3216 | 15 ± 2 | 40 ± 5 | 22 ± 1 | 16 ± 0.2 |
| C-3218 | 200 ± 3 | 200 ± 1 | 64 ± 5 | 137 ± 14 |
| C-3220 | 5.9 ± 1.1 | 56 ± 4 | 45 ± 9 | 35 ± 6 |
| C-3256 | 215 ± 5 | 205 ± 29 | 8.9 ± 1.6 | 2.8 ± 3.2 |
| C-3262 | 3.8 ± 0.3 | 13.5 ± 0.8 | 6.8 ± 0.8 | 7.2 ± 0.8 |
| C-3263 | 7.6 ± 0.2 | 29 ± 0.8 | 9.1 ± 0.5 | 17 ± 0.2 |
| C-3270 | 21 ± 3 | 87 ± 4 | 52 ± 5 | 33 ± 4 |
| C-3271 | 49 ± 6 | 138 ± 11 | 13 ± 2 | 54 ± 4 |
| C-3272 | 4.5 ± 0.9 | 57 ± 6 | 8.4 ± 0.9 | 26 ± 0.4 |
| C-3273 | 31 ± 0.9 | 56 ± 12 | 35 ± 3 | 92 ± 2 |
| C-3281 | 164 ± 3.2 | 125 ± 6.4 | 15 ± 1 | 118 ± 5 |
| C-3287 | 92 ± 9.2 | 144 ± 6 | 12 ± 2 | 123 ± 17 |
| C-3288 | 70 ± 2.9 | 118 ± 3 | 10 ± 1 | 113 ± 4 |
| C-3290 | 9.5 ± 1.8 | 6.9 ± 0.2 | 7.8 ± 1.6 | 29 ± 4 |
| C-3291 | 140 ± 3 | 140 ± 5 | 32 ± 4 | 34 ± 1 |
| C-3292 | 34 ± 3.4 | 14.4 ± 1.4 | 16 ± 1 | 25 ± 1 |
| C-3294 | 88.5 ± 11 | 8.1 ± 0.7 | 40 ± 6 | 49 ± 6 |
| C-3295 | 74.1 ± 2.5 | 12 ± 1.1 | 17 ± 1 | 32 ± 2 |
| C-3296 | 210 ± 15 | 37 ± 1.5 | 30 ± 1 | 32 ± 1 |
| C-3297 | 154 ± 11 | 15.4 ± 0.7 | 5.6 ± 0.6 | 7.5 ± 0.5 |
| C-3299 | 56 ± 3 | 53 ± 7 | 18 ± 2 | 41 ± 2 |
| C-3303 | 70 ± 2 | 27 ± 2 | 102 ± 9 | 170 ± 35 |
| C-3304 | 17 ± 3 | 10 ± 1 | 13 ± 1 | 49 ± 1 |
| C-3305 | 190 ± 3 | 21 ± 1 | 12 ± 1 | 25 ± 1 |
| C-3308 | 120 ± 6 | 100 ± 5 | >500 | 485 ± 32 |
| C-3311 | 5.1 ± 0.2 | 7.2 ± 0.2 | 33 ± 4 | 124 ± 5 |
| C-3314 | 4.5 ± 1 | 14 ± 0.8 | 104 ± 3 | 206 ± 21 |
| C-3316 | 76 ± 3 | 81 ± 4 | 78 ± 12 | 137 ± 18 |
| C-3319 | 44 ± 4 | 31 ± 6 | 25 ± 5 | 28 ± 8 |
| C-3320 | 180 ± 8 | 78 ± 19 | 380 ± 15 | >500 |
| C-3324 | 510 ± 3 | 27 ± 3 | 102 ± 12 | 156 ± 9 |
| C-3326 | 100 ± 5 | 170 ± 20 | 169 ± 20 | 349 ± 13 |
| C-3327 | 130 ± 10 | 150 ± 10 | 161 ± 2 | 168 ± 23 |
| C-3329 | 33 ± 4 | 19 ± 2 | 6.5 ± 0.5 | 8.2 ± 0.8 |
| C-3332 | 140 ± 20 | 5.9 ± 0.3 | 44 ± 7 | 28 ± 3 |
| C-3336 | 4.6 ± 0.4 | 0.5 ± 0.1 | 7.6 ± 1.9 | 16 ± 3 |
| C-3342 | 6.7 ± 2 | 6 ± 0.5 | 17 ± 2 | 33 ± 2 |
| C-3343 | 6.5 ± 0.6 | 68 ± 4 | 26 ± 8 | 46 ± 5 |
| C-3346 | 169 ± 11 | 17 ± 2 | >200 | 458 ± 6 |
| C-3350 | 16 ± 5 | 49 ± 5 | 136 ± 6 | 80 ± 8 |
| C-3353 | 31 ± 1 | >500 | 92 ± 8 | 53 ± 9 |
| C-3355 | 20 ± 1 | 39 ± 1 | 247 ± 14 | 276 ± 9 |

TABLE 5-continued

The in vitro antiproliferative effect of PDI A3 inhibitors towards panel of cancer cells (48-hour exposition)

| Comp. | Cytotoxicity, IC50, μM HT-1080 | CaCo-2 | MDA-MB-231 | MCF-7 |
|---|---|---|---|---|
| C-3357 | 30 ± 1 | 61 ± 3 | 25 ± 6 | 295 ± 9 |
| C-3362 | 32 ± 5 | 25 ± 6 | 19.1 ± 1 | 40 ± 9 |
| C-3364 | 29 ± 4 | 11 ± 3 | 21 ± 0.3 | 22 ± 2 |
| C-3365 | 28 ± 4 | 21 ± 4 | 4.6 ± 0.1 | 7.3 ± 0.5 |
| C-3366 | 11 ± 2 | 11 ± 2 | 20 ± 0.2 | 9.1 ± 0.6 |
| C-3368 | 28 ± 1 | 28 ± 5 | 26 ± 3 | 16 ± 4 |
| C-3369 | 10 ± 2 | 22 ± 1 | 22 ± 2 | 21 ± 1 |
| C-3371 | 15 ± 3 | 25 ± 1 | 36 ± 7 | 11 ± 1 |
| C-3373 | 4.8 ± 0.8 | 43 ± 6 | 19 ± 1 | 19 ± 2 |
| C-3374 | 4.6 ± 0.3 | 25 ± 5 | 6.7 ± 0.2 | 4.9 ± 0.6 |
| C-3375 | 22 ± 4 | 55 ± 5 | 75 ± 4 | 12 ± 2 |
| C-3376 | 1.3 ± 0.1 | 11 ± 1 | 2.3 ± 0.2 | 27 ± 2 |
| C-3377 | 6.1 ± 0.3 | 16 ± 1 | 7.8 ± 1.4 | 4.8 ± 0.1 |
| C-3380 | 28 ± 4 | 157 ± 25 | 32 ± 7 | 44 ± 10 |
| C-3383 | 12 ± 1 | 50 ± 7 | 7.3 ± 0.5 | 80 ± 6 |
| C-3384 | 14 ± 3 | 56 ± 6 | 5.5 ± 0.6 | 40 ± 5 |
| C-3385 | 8.0 ± 0.7 | 20 ± 2 | 7.0 ± 0.7 | 16 ± 3 |
| C-3389 | 36 ± 3 | 49 ± 2 | 32 ± 3 | 47 ± 6 |
| C-3390 | 7.9 ± 0.9 | 11 ± 2 | 18 ± 0.1 | 20 ± 0.3 |
| C-3391 | 7.8 ± 1.0 | 38 ± 4 | 20 ± 0.3 | 22 ± 2 |
| C-3393 | 0.46 ± 0.04 | 35 ± 1 | 32 ± 4 | 29 ± 3 |
| C-3397 | 9.3 ± 1.7 | 36 ± 5 | 38 ± 2 | 62 ± 4 |
| C-3398 | 7.4 ± 0.8 | 34 ± 6 | 17 ± 3 | 23 ± 3 |
| C-3399 | 7.9 ± 0.7 | 55 ± 7 | 17 ± 1 | 41 ± 6 |
| C-3400 | 11 ± 1 | 24 ± 2 | 24 ± 5 | 33 ± 1 |
| C-3402 | 4.6 ± 0.1 | 14 ± 2 | 39 ± 5 | 43 ± 8 |
| C-3403 | 6.7 ± 0.9 | 38 ± 5 | 16 ± 1 | 11 ± 3 |
| C-3427 | 5.9 ± 0.5 | 20 ± 5 | 9.3 ± 1 | 13 ± 2 |
| C-3459 | >500 | n.e. | n.e. | n.e. |
| C-3511 | n.t. | 61 ± 4 | 5.4 ± 0.3 | 28 ± 3 |
| C-3517 | n.t. | 74 ± 4 | 12 ± 1 | 18 ± 1 |
| C-3520 | n.t. | 45 ± 6 | 16 ± 2 | 30 ± 1 |
| C-3532 | 74 ± 1 | 181 ± 33 | 27 ± 2 | 103 ± 2 |
| C-3535 | 84 ± 3 | 35 ± 7 | 107 ± 11 | 81 ± 0 |
| C-3537 | 17 ± 1 | 27 ± 2 | 28 ± 3 | 35 ± 1 |
| C-3539 | 20 ± 1 | 23 ± 1 | 40 ± 5 | 113 ± 6 |
| C-3546 | 0.13 ± 0.02 | 73 ± 10 | 14 ± 1 | 32 ± 7 |
| C-3548 | 9.2 ± 1.0 | 45 ± 13 | 57 ± 9 | 37 ± 3 |
| C-3559 | 372 ± 23 | 260 ± 55 | 128 ± 8 | 154 ± 25 |
| C-3562 | 31 ± 2 | 36 ± 6 | 24 ± 2 | 57 ± 5 |
| C-3570 | 12 ± 1 | 13 ± 1 | 14 ± 3 | 29 ± 2 |
| C-3591 | 9.9 ± 0.9 | 27 ± 4 | 12 ± 3 | 16 ± 2 |
| C-3593 | 16 ± 1 | 25 ± 4 | 20 ± 1 | 9 ± 2 |
| C-3594 | 15 ± 1 | 7.2 ± 0.6 | 6.1 ± 2.4 | 10 ± 2 |

EXAMPLE 5. ANTIPROLIFERATIVE EFFECT OF PDIA3-INHIBITORS IN VITRO IN HYPOXIC CONDITIONS AND IN CANCER CELLS STIMULATED WITH ESTROGEN

Anticancer activity of selected compounds of invention, PDI A3-inhibitors has been also tested in vitro in antiproliferative assay in normoxic and hypoxic conditions as well in estrogen-stimulated cancer cells. In the experiment, cells were seeded on 96-well plates (Sarstedt, Germany) in appropriate culture medium at a density of $10^5$ cells/mL 24 h before adding the tested compounds. Cells were treated with each compound in four concentrations in the range 0.1-100 μg/mL. Cisplatin (Ebewe, Austria) in the range 0.01-10 μg/mL was used as a reference drug. Dimethyl sulfoxide (DMSO), used as a stock solution solvent, was tested for antiproliferative activity and it did not affect cell proliferation at 0.1% (v/v)—a highest concentration used in compound solutions. After 72 h of compound treatment at 37° C., 5% $CO_2$ humid atmosphere and in wo different oxygen level conditions: 21%—normal and <1%—hypoxia. In some experiments the MDA-MB-231 and MCF-7 cells were seeded with or without 200 nM estradiol and after 24 h the tested compounds were added. A previously described sulforhodamine B antiproliferative assay was used with minor modifications (Skehan P et al., 1990). Briefly, cells were fixed with 50 μL/well of 50% (w/v) trichloroacetic acid (Avantor Performance Materials, Gliwice, Poland). After 1 h incubation, plates were washed several times with tap water and 50 μL of 0.4% (w/v) solution of sulforhodamine B (Sigma-Aldrich, Germany) in 1% (v/v) acetic acid (Avantor Performance Materials, Gliwice, Poland) was added to each well. After 30 min incubation at room temperature, unbound dye was washed out with 1% (v/v) acetic acid, whereas bound dye was solubilized with 10 mM unbuffered TRIS (Avantor Performance Materials, Gliwice, Poland) solution. The entire procedure was performed using a BioTek EL-406 washing station (BioTek Instruments, USA). After additional 30 min, absorbance was read using a Biotek Hybrid H4 reader (BioTek Instruments, USA) at 540 nm wavelength. MTT assay was used alternatively for HL-60 cell line and in the experiment in which estrogens are added (specified in the table legend). Absorbance was measured using a Biotek Hybrid H4 reader at 570 nm wavelength for MTT assay.

Compounds at each concentration were tested in triplicate in a single experiment and each experiment was repeated at least three times independently. Results of in vitro antiproliferative effects are shown in Table 3 and Table 4. Results are presented as mean $IC_{50}$±SD.

TABLE 3

Antiproliferative effect of PDI A3 inhibitors in normal (21% of oxygen) and hypoxia (<1% of oxygen) conditions against human cancer cell lines (72 hours exposition).

| Compd | Cell line/condition IC50 [μg/ml] MCF-7 normal | MCF-7 hypoxia | MDA-MB-231 normal | MDA-MB-231 hypoxia | Caco-2 normal | HT-29 normal |
|---|---|---|---|---|---|---|
| C-3216 | 3.7 ± 0.4 | 3.6 ± 0.3 | 5.0 ± 1.4 | 6.2 ± 3.7 | 4.5 ± 0.8 | 5.6 ± 0.9 |
| CCF642 | 0.7 ± 0.5 | 0.6 ± 0.6 | 0.3 ± 0.1 | 0.3 ± 0.2 | 0.4 ± 0.1 | 0.4 ± 0.05 |
| LOC14 | 4.4 ± 0.9 | 3.9 ± 0.3 | 2.8 ± 0.4 | 2.6 ± 0.5 | 9.1 ± 3.4 | 12.6 ± 8.4 |
| Cisplatin | 1.8 ± 0.3 | 1.3 ± 0.5 | 3.2 ± 0.5 | 3.1 ± 0.9 | 2.3 ± 0.5 | 2.82 ± 0.6 |

TABLE 4

The antiproliferative effect of PDI A3 inhibitors towards human breast cancer cell lines pretreated or not with estradiol and for comparison towards human colon cancer and leukemia cell line (72 hours exposition).

| | Cell line/condition IC50 [μg/ml] | | | | | | Selectivity index (SI): IC50 of |
|---|---|---|---|---|---|---|---|
| | MDA-MB-231 | | MCF-7 | | HT-29 | HL-60 | MCF-10A/IC50 |
| Cmpd | normal | +estradiol | normal | +estradiol | normal | normal | of MCF-7 |
| C-3373 | 3.2 ± 0.1 | 3.2 ± 0.3 | 3.3 ± 0.1 | 2.6 ± 0.5 | 33.4 ± 1.1 | 3.1 ± 0.1 | 1.20 |
| C-3375 | 3.8 ± 0.1 | 7.0 ± 1.1* | 3.5 ± 0.4 | 3.4 ± 0.3 | 27.8 ± 7.5 | 3.3 ± 0.2 | 6.90 |
| C-3390 | 3.2 ± 0.2 | 9.4 ± 3.5 | 3.2 ± 0.3 | 3.4 ± 0.3 | 33.6 ± 2.9 | 14.4 ± 0.7 | 5.10 |
| C-3399 | 2.9 ± 0.3 | 6.4 ± 1.9 | 3.7 ± 0.3 | 4.3 ± 0.3 | 4.3 ± 0.2 | 2.4 ± 0.3 | 1.6 |

Statistical analysis: Unpaired t test.
*$p < 0.05$ as compared to appropriate cells not pretreated with estradiol.
MTT assay was used for antiproliferative activity assessment.

In reference to Table 3 and Table 4, all new compounds tested in normal condition revealed antiproliferative activity comparable to LOC14. In reference to Table 3, the antiproliferative effect of C-3216 and reference inhibitors was comparable and normoxic and hypoxic conditions supporting the notion that antiproliferative effect of compounds of invention on human breast cancer cells MCF-7 and MDA-MB-231 is not dependent on oxygen access. Therefore, these compounds are effective in the hypoxic environment that occurs in the tumor. In reference to Table 4, it was established that the MDA-MB-231 line after treatment with estradiol (200 nM) shows slightly lower sensitivity to PDI A3 inhibitors: C-3375, C-3390, C-3399, a phenomenon that was not observed in MCF-7 breast cancer cell line.

EXAMPLE 6. EVALUATION OF EFFECTS OF PDI A3 INHIBITORS ON TRANSENDOTHELIAL CANCER CELLS MIGRATION IN VITRO

To assess whether compounds of invention, PDI A3-inhibitors are also effective as inhibitors of cancer cell transmigration through endothelium the transmigration assay with MDA-MB-231/lung microvascular endothelium was used as described previously (Stojak et al., 2018). Cell migration was assayed in 24-well, 6.5-mm internal-diameter Transwell plates (8.0 μm pore size; BD Pharmingen). Human lung microvascular endothelial cells (hLMVECs) were seeded into 24-well plates (seeding density 5×104 cells/insert) on the upper side of the filter and left to grow to confluence. After confluent monolayer formation, hLMVECs were pre-treated with 10 ng/mL IL-1β for 6 h. Prior to use in transmigration assay, cancer cells were pre-incubated with various concentrations (3, 10, 30, 50, 100 μM) of tested inhibitors of PDIA3, C-3390, C-3399 for 30 min. Then, MDA-MB-231 cells (each 5×104 per well) were placed into upper chambers and tested PDI inhibitors at various concentrations (1, 10, 30, 50, 100 μM) were given. Lower chambers were filled with medium containing chemoattractant (20% FBS or 100 ng/mL SDF-1α). After 24 h of co-culture, hLMVEC monolayers and non-migrating cancer cells on the upper surface of the membrane were removed. Migrated cancer cells on the undersides of the Transwell membranes were detached and stained by Calcein-AM-Accutase solution for 60 minutes. The cell number was determined by measuring the fluorescence using plate reader. Experiments were performed in triplicates and repeated three times.

Figure 6:
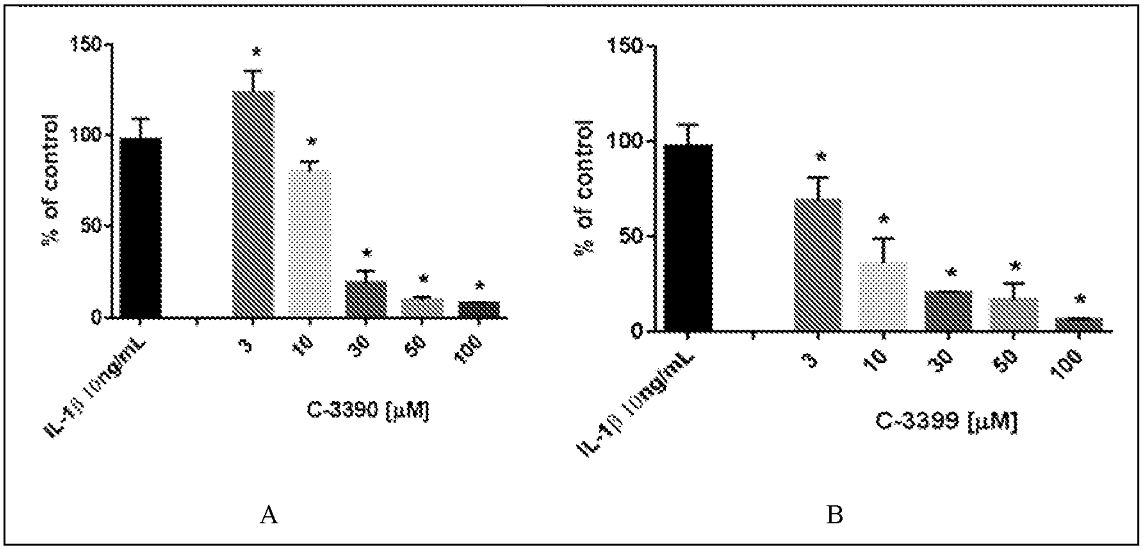
FIG. 6 shows effect of C-3399 (A) and C-3399 (B) on MDA-MB-231 cell transendothelial migration across endothelial monolayer.

In reference to FIG. 6*a*, compound of invention C-3390 inhibited MDA-MB-231 cell transmigration across IL-1β 10 ng/mL (6 hours)—stimulated hLMVECs, in a concentration-dependent manner The number of migrating MDA-MB-231 cells through the hLMVEC monolayer was quantified by measuring the fluorescence, as described in Methodology. Data represent mean±SD of three independent experiments. Statistical analysis was performed using one-way ANOVA. Symbols mark the statistical significance levels as follows: (*) indicates $p<0.05$ as compared to IL-1β 10 ng/mL-stimulated group In reference to FIG. 6*b*, compound of invention C-3399 inhibited MDA-MB-231 cell transmigration across IL-1β 10 ng/mL (6 hours)-stimulated hLMVECs, in a concentration-dependent manner. The number of migrating MDA-MB-231 cells through the hLMVEC monolayer was quantified by measuring the fluorescence, as described in Methodology. Data represent mean±SD of three independent experiments. Statistical analysis was performed using one-way ANOVA. Symbols mark the statistical significance levels as follows: (*) indicates $p<0.05$ as compared to IL-1β 10 ng/mL-stimulated group Therefore, tested compounds inhibitors of PDIA3 inhibited transmigration of breast cancer cells across hLMVEC monolayer in a concentration-dependent manner.

BIBLIOGRAPHY

Atkin et al. (2008). Neurobiol Dis 30(3):400-407.
Bennett et al. (2000). J. Immunol. 164(8), 4120-4129
Burgess et al. (2000). J. Biol Chem. 275(13):9758-9766;
Cho et al. (2008). J Clin Invest 118(3):1123-1131.
Colla et al. (2012). J Neurosci 32(10):3306-3320.
Darby and Creighton (1995). Biochemistry. 34(37):11725-11735.
Essex et al. (1999). Br J. Haematol. 104(3):448-454;
Ge et al. (2013). ACS Chem Biol 8(11):2577-2585.
Hashida et al. (2011). J Toxicol Sci 36(1):1-7.
Hatahet et al. (2009). Antioxid Redox Signal. 11(11), 2807-2850
Hayashi et al. (2008). Pflugers Arch. 456:1239-1251.
Hettinghouse A (2018). Pharmacol Ther. 2018 January; 181:34-48.
Hotchkiss et al. (1998). Biochim Biophys Acta. 1388(2), 478-488;
Jasuja et al. (2010). Blood 116(22), 4665-4674
Jasuja et al. (2012). J Clin Invest 122(6):2104-2113.
Karala et al. (2010). FEBS J. 277(11), 2454-2462

Khan et al. (2011). ACS Chem. Biol. 6(3), 245-251
Koivu et al. (1987). J Biol Chem 262(14):6447-6449.
Kramkowski et al. (2012). Arterioscler Thromb Vase Biol. 32:2149-2157.
Lovat et al. (2008). Cancer Res 68(13):5363-5369.
Manickam et al. (2008). Br J Haematol. 140(2), 223-229.
Milczarek et al. (2014). Oncol Rep. 32:491-504.
Reinhardt et al. (2008). J. Clin Invest. 118(3), 1110-1122
Rossowska et al. (2017) Front Immunol. 8:713.
Stojak et al., (2018). Pharmacol Res. 136:160-171
Wetterau et al. (1990). J Biol Chem 265(17):9800-9807.
Xu et al. (2012). Proc Natl Acad Sci USA 109(40):16348-16353.
Yang Z et al. (2018). Onco Targets Ther. 2018; 11:4159-4166.
Yoo et al. (2002). Neurosci Lett 334(3):196-200.

The invention claimed is:

1. An N,N-disubstituted aromatic sulphonamide, wherein the N,N-disubstituted aromatic sulphonamide is selected from the group consisting of:

Methyl 1-(4-butoxyphenyl)sulfonylaziridine-2-carboxylate;

1-(4-Nitrophenyl)sulfonylaziridine-2-carboxamide;

Methyl 1-(4-butylphenyl)sulfonylaziridine-2-carboxylate;

Methyl 1-[[6-(dimethylamino)-5-formyl-2-naphthyl]sulfonyl]aziridine-2-carboxylate; and Methyl 1-[[5-(dimethylamino)-2-naphthyl]sulfonyl]aziridine-2-carboxylate.

* * * * *